(12) United States Patent
Mujeeb-U-Rahman et al.

(10) Patent No.: US 10,376,146 B2
(45) Date of Patent: Aug. 13, 2019

(54) MINIATURIZED IMPLANTABLE ELECTROCHEMICAL SENSOR DEVICES

(71) Applicant: California Institute of Technology, Pasadena, CA (US)

(72) Inventors: Muhammad Mujeeb-U-Rahman, Pasadena, CA (US); Axel Scherer, Barnard, VT (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 557 days.

(21) Appl. No.: 14/174,827

(22) Filed: Feb. 6, 2014

(65) Prior Publication Data

US 2014/0228660 A1   Aug. 14, 2014

Related U.S. Application Data

(60) Provisional application No. 61/761,504, filed on Feb. 6, 2013.

(51) Int. Cl.
| | | |
|---|---|---|
| *A61B 5/00* | (2006.01) | |
| *A61B 5/1473* | (2006.01) | |
| *A61B 5/145* | (2006.01) | |
| *A61B 5/1486* | (2006.01) | |

(52) U.S. Cl.
CPC .......... *A61B 5/0026* (2013.01); *A61B 5/0031* (2013.01); *A61B 5/1473* (2013.01); *A61B 5/14532* (2013.01); *A61B 5/14865* (2013.01); *A61B 2560/0219* (2013.01); *A61B 2562/028* (2013.01); *A61B 2562/0209* (2013.01); *A61B 2562/04* (2013.01); *A61B 2562/125* (2013.01)

(58) Field of Classification Search
CPC . A61B 5/0026; A61B 5/0031; A61B 5/14865; A61B 5/1473; A61B 5/14532; A61B 2562/125; A61B 2560/0219; A61B 2562/0209; A61B 2562/028; A61B 2562/04
See application file for complete search history.

(56) References Cited

U.S. PATENT DOCUMENTS

| | | | |
|---|---|---|---|
| 3,536,386 | A | 10/1970 | Spivack |
| 4,129,628 | A | 12/1978 | Tamutus |
| 5,302,540 | A | 4/1994 | Ko et al. |

(Continued)

FOREIGN PATENT DOCUMENTS

| | | |
|---|---|---|
| EP | 2433563 | 3/2012 |
| JP | H05215712 A | 8/1993 |

(Continued)

OTHER PUBLICATIONS

Seese, T.M., et al., "Characterization of tissue morphology, angiogenesis, and temperature in the adaptive response of muscle tissue in chronic heating", Laboratory Investigation, 1998; 78 (12): pp. 1553-1562.

(Continued)

*Primary Examiner* — Tiffany Weston
(74) *Attorney, Agent, or Firm* — Steinfl + Bruno LLP

(57) ABSTRACT

An implantable device having a communication system, a sensor, and a monolithic substrate is described. The monolithic substrate has an integrated sensor circuit configured to process input from the sensor into a form conveyable by the communication system.

15 Claims, 20 Drawing Sheets

(56) References Cited

U.S. PATENT DOCUMENTS

| | | | |
|---|---|---|---|
| 5,482,882 A | 1/1996 | Lur et al. | |
| 5,614,875 A | 3/1997 | Jang et al. | |
| 5,711,861 A | 1/1998 | Ward et al. | |
| 5,797,898 A | 8/1998 | Santini, Jr. et al. | |
| 5,812,065 A | 9/1998 | Schrott et al. | |
| 5,999,849 A | 12/1999 | Gord et al. | |
| 6,123,861 A | 9/2000 | Santini, Jr. et al. | |
| 6,259,937 B1 * | 7/2001 | Schulman | A61B 5/14532 600/300 |
| 6,402,689 B1 | 6/2002 | Scarantino et al. | |
| 6,504,292 B1 | 1/2003 | Choi et al. | |
| 6,560,471 B1 * | 5/2003 | Heller | A61B 5/0002 600/309 |
| 6,864,802 B2 | 3/2005 | Smith et al. | |
| 7,348,243 B2 | 3/2008 | Kim | |
| 7,741,664 B2 | 6/2010 | Choi et al. | |
| 7,800,078 B2 | 9/2010 | Colvin, Jr. et al. | |
| 8,123,687 B2 | 2/2012 | Dacquay et al. | |
| 8,421,082 B1 | 4/2013 | Yang | |
| 8,527,025 B1 | 9/2013 | Shults et al. | |
| 8,681,885 B2 | 3/2014 | Chung et al. | |
| 9,006,014 B2 | 4/2015 | Mujeeb-U-Rahman et al. | |
| 9,173,605 B2 | 11/2015 | Mujeeb-U-Rahman et al. | |
| 9,177,933 B2 | 11/2015 | Mujeeb-U-Rahman et al. | |
| 2001/0051787 A1 | 12/2001 | Haller et al. | |
| 2002/0049389 A1 | 4/2002 | Abreu | |
| 2002/0072784 A1 | 6/2002 | Sheppard, Jr. et al. | |
| 2002/0172820 A1 | 11/2002 | Majumdar et al. | |
| 2003/0130616 A1 * | 7/2003 | Steil | A61B 5/14532 604/66 |
| 2004/0073137 A1 | 4/2004 | Lloyd et al. | |
| 2004/0127012 A1 | 7/2004 | Jin | |
| 2004/0206916 A1 | 10/2004 | Colvin, Jr. et al. | |
| 2005/0142771 A1 | 6/2005 | Kim | |
| 2005/0161826 A1 | 7/2005 | Shah et al. | |
| 2005/0218398 A1 | 10/2005 | Tran | |
| 2005/0219398 A1 | 10/2005 | Sato et al. | |
| 2005/0261563 A1 | 11/2005 | Zhou et al. | |
| 2006/0047283 A1 | 3/2006 | Evans, III et al. | |
| 2006/0131695 A1 | 6/2006 | Kuekes et al. | |
| 2006/0157701 A1 | 7/2006 | Bauer et al. | |
| 2006/0189963 A1 | 8/2006 | Richards et al. | |
| 2006/0247539 A1 | 11/2006 | Schugt et al. | |
| 2006/0261406 A1 | 11/2006 | Chen | |
| 2007/0145830 A1 | 6/2007 | Lee et al. | |
| 2007/0152248 A1 | 7/2007 | Choi et al. | |
| 2008/0154101 A1 * | 6/2008 | Jain | A61B 5/0017 600/309 |
| 2008/0224122 A1 | 9/2008 | Saitoh et al. | |
| 2008/0303152 A1 | 12/2008 | Zhang | |
| 2009/0203980 A1 | 8/2009 | Carlson et al. | |
| 2009/0220561 A1 | 9/2009 | Jin et al. | |
| 2010/0102380 A1 | 4/2010 | Ohlsson et al. | |
| 2010/0114225 A1 | 5/2010 | Imran et al. | |
| 2010/0151604 A1 | 6/2010 | Kal et al. | |
| 2010/0215543 A1 | 8/2010 | Henry et al. | |
| 2010/0249548 A1 | 9/2010 | Mueller | |
| 2010/0261343 A1 | 10/2010 | Mizukoshi et al. | |
| 2011/0031470 A1 | 2/2011 | Scherer et al. | |
| 2011/0042237 A1 * | 2/2011 | Fukuda | B01L 3/5027 205/775 |
| 2011/0045660 A1 | 2/2011 | Romano et al. | |
| 2011/0116089 A1 | 5/2011 | Schmidt et al. | |
| 2011/0233512 A1 | 9/2011 | Yang et al. | |
| 2012/0088258 A1 | 4/2012 | Bishop et al. | |
| 2012/0101540 A1 | 4/2012 | O'Brien et al. | |
| 2012/0116683 A1 | 5/2012 | Potyrailo et al. | |
| 2012/0150004 A1 | 6/2012 | Currie et al. | |
| 2012/0187375 A1 | 7/2012 | Guo et al. | |
| 2012/0226118 A1 | 9/2012 | Delbeke et al. | |
| 2012/0323218 A1 | 12/2012 | Pang et al. | |
| 2013/0194540 A1 | 8/2013 | Pugh et al. | |
| 2013/0342898 A1 | 12/2013 | Alvine et al. | |
| 2014/0001110 A1 | 1/2014 | Lee et al. | |
| 2014/0011013 A1 | 1/2014 | Jin et al. | |
| 2014/0048773 A1 | 2/2014 | Chang et al. | |
| 2014/0057416 A1 | 2/2014 | Warren et al. | |
| 2014/0083872 A1 | 3/2014 | Fuerst et al. | |
| 2014/0163338 A1 | 6/2014 | Roesicke | |
| 2014/0290057 A1 | 10/2014 | Lin et al. | |
| 2014/0379090 A1 | 12/2014 | Diomidis et al. | |
| 2015/0057516 A1 | 2/2015 | Mujeeb-U-Rahman et al. | |
| 2017/0020415 A1 | 1/2017 | Scherer et al. | |
| 2017/0020416 A1 | 1/2017 | Scherer et al. | |

FOREIGN PATENT DOCUMENTS

| | | |
|---|---|---|
| JP | H06140569 A | 5/1994 |
| JP | H1074710 A | 3/1998 |
| JP | H10121237 A | 5/1998 |
| JP | 2004147845 A | 5/2004 |
| JP | 2005197704 A | 7/2005 |
| JP | 2006126112 A | 5/2006 |
| JP | 2010127757 A | 6/2010 |
| JP | 2010529681 A | 8/2010 |
| JP | 2012500476 A | 1/2012 |
| JP | 2012531751 A | 12/2012 |
| KR | 10-2005-0066741 A | 6/2005 |
| KR | 1020070073430 A | 7/2007 |
| KR | 100869123 B1 | 11/2008 |
| KR | 1020090067533 A | 6/2009 |
| KR | 1020090098285 A | 9/2009 |
| KR | 100964574 B1 | 6/2010 |
| KR | 20110041215 A | 4/2011 |
| WO | 00/59370 | 10/2000 |
| WO | 2009/104132 A1 | 8/2009 |
| WO | 2010/019887 A1 | 2/2010 |
| WO | 2010/057051 A2 | 5/2010 |
| WO | 2010/075479 | 7/2010 |
| WO | 2010/075479 A3 | 10/2010 |
| WO | 2010/151604 A2 | 12/2010 |
| WO | 2012/170837 A2 | 12/2012 |
| WO | 2014/093938 A1 | 6/2014 |
| WO | 2014/124184 A1 | 8/2014 |
| WO | 2015/013552 A1 | 1/2015 |

OTHER PUBLICATIONS

Ward, K. W., "A Review of the Foreign-body Response to Subcutaneously-implanted Devices: The Role of Macrophages and Cytokines in Biofouling and Fibrosis", *Journal of Diabetes Science and Technology*, vol. 2 (5), Sep. 2008, pp. 768-777.

Ward, K.W., et al., "The effect of microgeometry, implant thickness and polyurethane chemistry on the foreign body response to subcutaneous implants", *Biomaterials*, vol. 23, 2002, pp. 4185-4192.

Henry, M.D., et al., "Alumina Etch masks for Fabrication of High-Aspect-Ratio Silicon Micropillars and Nanopillars", Nanotechnology, 2009, 20 (25), 255305, 4 pages.

Ming Li, Chang; Dong, Hua; Cao, Xiaodong; T. Luong, John H.; Zhang, Xueji, "Implantable Electrochemical Sensors for Biomedical and Clinical Applications: Progress, Problems, and Future Possibilities," Current Medicinal Chemistry, 2007, vol. 14, Issue 8, pp. 937-951 (15).

Guigen Zhang, Chapter 13 "Design and Fabrication of 3D Skyscraper Nanostructures and Their Application in Biosensors" in *New Perspectives in Biosensors Technology and Applications*, Prof. Pier Andrea Serra (2011 Ed.), ISBN: 978-953-307-448-1, InTech Publishers, pp. 269-290.

Brian S. Ferguson et al., "Integrated Microfluidic Electrochemical DNA Sensor," Anal. Chem. 2009, 81, pp. 6503-6508.

Fang Wei, Peter B. Lillehoj, and Chih-Ming Ho,"DNA Diagnostics: Nanotechnology-Enhanced Electrochemical Detection of Nucleic Acids," Pediatric Research, May 2010; 67(5): pp. 458-468.

Syed M. Usman Ali et al., "Wireless Remote Monitoring of Glucose Using a Functionalized ZnO Nanowire Arrays Based Sensor," Sensors 2011, 11, pp. 8485-8496.

PCT International Search Report dated May 26, 2014 for PCT Application PCT/US2014/015177 filed on Feb. 6, 2014 in the name of California Institute of Technology.

(56) References Cited

OTHER PUBLICATIONS

PCT Written Opinion dated May 26, 2014 for PCT Application PCT/US2014/015177 filed on Feb. 6, 2014 in the name of California Institute of Technology.
Ahmadi, M.M. et al. "A Wireless-Implantable Microsystem for Continuous Blood Glucose Monitoring" Transaction on Biomedical Circuits and Systems, Jun. 2009, vol. 3, No. 3, pp. 169-180.
Freckmann, G. et al. "Performance Evaluation of Three Continuous Glucose Monitoring Systems: Comparison of Six Sensors Per Subject in Parallel" Journal of Diabetes Science and Technology, Jul. 2013, vol. 7, No. 4, pp. 842-853.
Liao, Y.T. et al. "A 3um CMOS Glucose Sensor for Wireless Contact-Lens Tear Glucose Monitoring" Journal of Solid-State Circuits, Jan. 2012, vol. 47, No. 1, pp. 335-344.
PCT International Search Report for PCT/US2013/075192 filed on Dec. 13, 2013 in the name of California Institute of Technology, dated Apr. 30, 2014.
PCT International Search Report for PCT/US2013/048087 filed on Dec. 13, 2013 in the name of California Institute of Technology, dated Apr. 30, 2014.
PCT Written Opinion for PCT/US2013/075192 filed on Dec. 13, 2013 in the name of California Institute of Technology, dated Apr. 30, 2014.
PCT Written Opinion for PCT/US2014/048087 filed on Jul. 24, 2014 in the name of California Institute of Technology, dated Nov. 11, 2014.
O'Driscoll et al., "A mm-sized implantable power receiver with adaptive link compensation", International Solid-State Circuits Conference, pp. 294-295, 2009.
Yao et al. "A contact lens with embedded sensor for monitoring tear glucose level" Mar. 2011, Biosensors and Bioelectronics, 26(7) pp. 3290-3296.
Restriction Requirement for U.S. Appl. No. 14/106,701, filed Dec. 13, 2013 on behalf of California Institute of Technology, dated Nov. 20, 2014. 6 pages.
Notice of Allowance for U.S. Appl. No. 14/106,701, filed Dec. 13, 2013 on behalf of California Institute of Technology, dated Jan. 29, 2015. 11 pages.
Non-Final Office Action for U.S. Appl. No. 14/340,498, filed Jul. 24, 2014 on behalf of California Institute of Technology, dated Jun. 25, 2015. 7 pages.
Notice of Allowance for U.S. Appl. No. 14/340,498, filed Jul. 24, 2014 on behalf of California Institute of Technology, dated Sep. 11, 2015. 5 pages.
Notice of Allowance for U.S. Appl. No. 14/656,650, filed Mar. 12, 2015 on behalf of California Institute of Technology, dated Sep. 18, 2015. 9 pages.
Non-Final Office Action for U.S. Appl. No. 14/465,777, filed Aug. 21, 2014 on behalf of California Institute of Technology, dated Nov. 29, 2016. 17 pages.
Final Office Action for U.S. Appl. No. 14/465,777, filed Aug. 21, 2014 on behalf of California Institute of Technology, dated May 17, 2017. 21 pages.
Akin, T., et al. "A wireless implantable multichannel digital neural recording system for a micromachined sieve electrode". *IEEE Journal of Solid-State Circuits*, 33(1), 109-118, 1998.

Mazhab-Jafari, H., et al. "16-Channel CMOS Impedance Spectroscopy DNA Analyzer With Dual-Slope Multiplying ADCs", *IEEE Transactions on Biomedical Circuits and Systems* 6(5), 468-478, (Oct. 2012).
Nazari, M., et al. "An Implantable Continuous Glucose Monitoring Microsystem in 0.18um CMOS." *Symposium on VLSI Circuits Digest of Technical Papers*, 2014. 2 pages.
European Search Report issued for Application No. 13861546.3, filed Dec. 13, 2013 on behalf of California Institute of Technology, dated Sep. 16, 2015. 10 pages.
European Search Report issued for Application No. 14749308.4, filed Feb. 6, 2014 on behalf of California Institute of Technology, dated Sep. 6, 2016. 13 pages.
European Search Report issued for Application No. 14829775.7, filed Jul. 24, 2014 on behalf of California Institute of Technology, dated Feb. 17, 2017. 12 pages.
Official Action for Russian Patent Application No. 2015122434/20(035100), filed Dec. 13, 2013 on behalf of California Institute of Technology, dated Oct. 2, 2015. 4 pages (Russian original + English translation).
Non-Final Office Action for U.S. Appl. No. 14/465,777, filed Aug. 21, 2014 on behalf of California Institute of Technology, dated Feb. 22, 2018.
Restriction Requirement issued for U.S. Appl. No. 15/216,662, filed Jul. 21, 2016 on behalf of California Institute of Technology, dated May 7, 2018. 6 pages.
Restriction Requirement issued for U.S. Appl. No. 15/216,675, filed Jul. 21, 2016 on behalf of California Institute of Technology, dated Mar. 26, 2018. 6 pages.
Non-Final Office Action for U.S. Appl. No. 15/216,675, filed Jul. 21, 2016 on behalf of California Institute of Technology, dated May 31, 2018. 24 pages.
Chang, S-W. et al., "Fabrication of Silicon Nanopillar-Based Nanocapacitor Arrays", Applied Physics Letters, vol. 96, No. 15, pp. 153108-1-153108-3, (2010), 4 pages.
Japanese Patent Office Official Office Action for Japanese Patent Application No. 2015-548024. Dispatch Date: Dec. 12, 2017. 16 pages. (English Translation + Japanese Original).
European Communication pursuant to Article 94(3) EPC for EP Application No. 14829775.7 filed Jul. 24, 2014 on behalf of California Institute of Technology, dated Mar. 8, 2018. 6 pages.
Japanese Office Action for Japanese Patent Application No. 2016-530056, dated Jun. 26, 2018. 13 pages (Japanese Original + English Translation).
Final Office Action for U.S. Appl. No. 14/465,777, filed Aug. 21, 2014 on behalf of California Institute of Technology, dated Sep. 18, 2018. 16 pages.
Final Office Action for U.S. Appl. No. 15/216,675, filed Jul. 21, 2016 on behalf of California Institute of Technology, dated Oct. 17, 2018. 11 pages.
Islam. M.T, et al., "Reduction of Specific Absorption Rate (SAR) in the Human Head With Ferrite Material and Metamaterial", Progress in Electromagnetics Research, vol. 9, pp. 47-58, (2009).
Non-Final Office Action for U.S. Appl. No. 15/216,662, filed Jul. 21, 2016 on behalf of California Institute of Technology, dated Oct. 1, 2018. 9 pages.

* cited by examiner

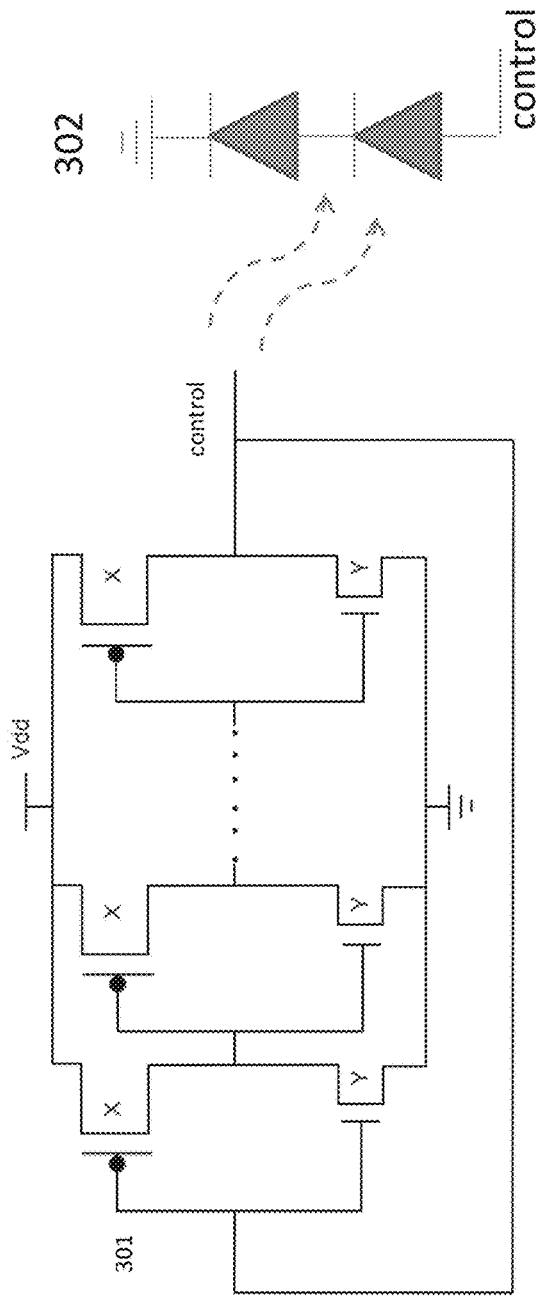
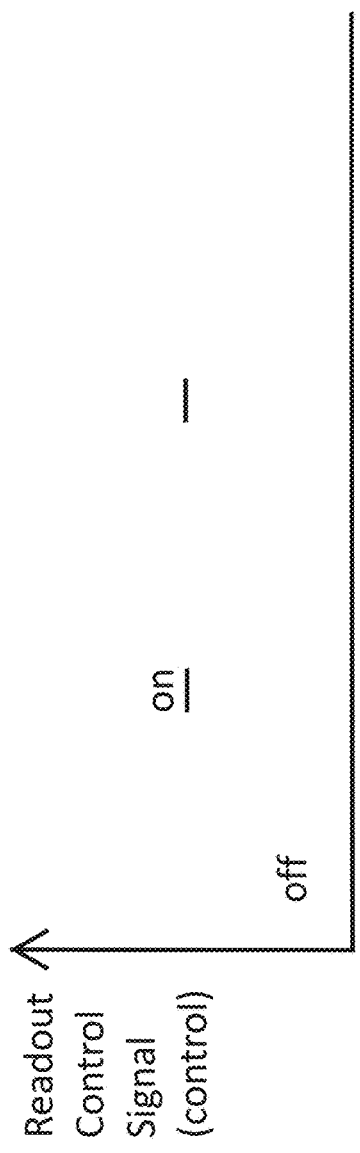
Figure 3A
Figure 3B

MINIATURIZED IMPLANTABLE ELECTROCHEMICAL SENSOR DEVICES

CROSS REFERENCE TO RELATED APPLICATIONS

The present application claims priority to U.S. Provisional application 61/761,504 filed on Feb. 6, 2013, which is incorporated herein by reference in its entirety. The present application is related to U.S. application Ser. No. 14/106,701 filed Dec. 13, 2013, herein incorporated by reference in its entirety.

TECHNICAL FIELD

The present disclosure relates to miniaturized implantable electrochemical sensor devices.

BACKGROUND

The measurement of biological indicators is of interest for a variety of medical disorders. Various systems have been developed to measure biological indicators from within the living body of various animals (e.g. mammals) via an implantable device.

Existing implantable devices have the potential to create high local temperatures inside the living body. Often power provided from external sources results in an increase in local temperature around the implantable device. Often transmission of information from the implantable device results in an increase in local temperature around the implantable device The living body, however, cannot tolerate high internal temperatures. High internal temperatures often lead to tissue death. (Seese, "Characterization of tissue morphology, angiogenesis, and temperature in the adaptive response of muscle tissue in chronic heating, Lab. Invest. 1998; 78 (12): 1553-62).

Another issue facing implantable devices is the formation of a foreign body capsule in the tissue of the living body around the implantable device. Fibrogen and other proteins bind to the device surface shortly after implantation in a process known as biofouling. Macrophages bind to the receptors on these proteins releasing growth factor β and other inflammatory cytokines. Procollagen is synthesized and becomes crosslinked after secretion into the extracellular space gradually contributing to formation of a dense fibrous foreign body capsule. The dense capsule prevents the implantable device from interfacing with the living body and thereby often hinders the operation of the implantable device (Ward, "A Review of the Foreign-body Response to Subcutaneously-implanted Devices: The Role of Macrophages and Cytokines in Biofouling and Fibrosis", Journal of Diabetes Science and Technology, Vol. 2, Is. 5, September 2008).

SUMMARY

In one embodiment the present disclosure relates to an implantable device comprising a communication system, a sensor, and a monolithic substrate comprising an integrated sensor circuit configured to process input from the sensor into a form conveyable by the communication system, and a an integrated power supply configured to receive energy from an external source.

In an alternative embodiment the invention relates a method for operating an implantable device comprising receiving pulsed power for a first interval of time at the implantable device and transmitting pulsed information for a second interval of time from the implantable device.

Various embodiments of the implantable device of the present enclosure receive power from an external device and transmit information to an external device while maintaining a low local temperature around the implantable device. Various embodiments of the implantable device of the present disclosure result in minimal foreign body capsule formation.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 3A illustrates an exemplary embodiment of control circuitry. FIG. 3B illustrates a graph for the control signal.

DETAILED DESCRIPTION

Figure 1:
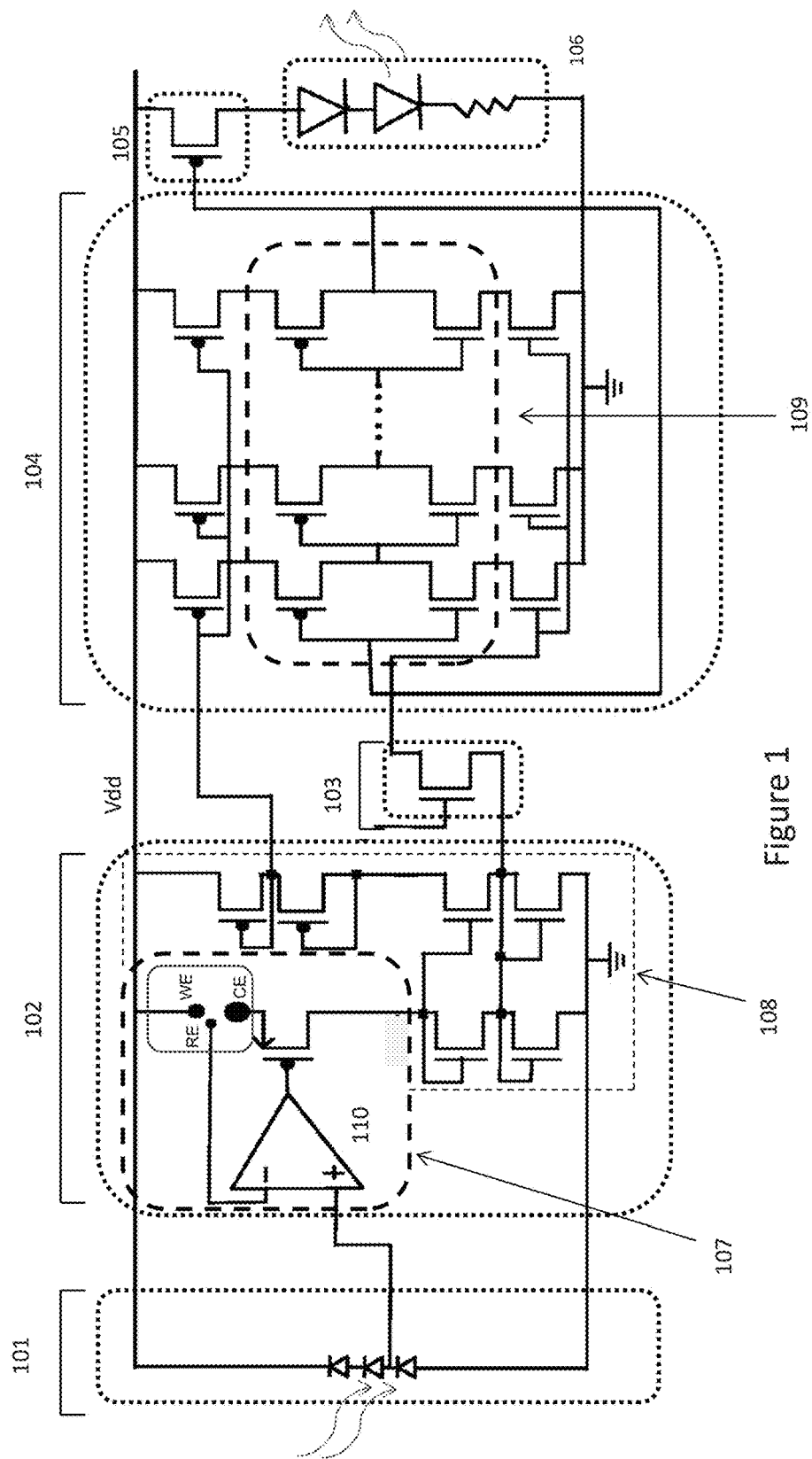
FIG. 1 illustrates an exemplary embodiment of the circuitry of the implantable device.

In an embodiment, the present disclosure relates to an implantable device including a communication system, a sensor and a monolithic substrate upon which a sensor circuit and a power supply are monolithically integrated wherein the communication system is located on a first face of the monolithic substrate and the integrated sensor is located on a second face of the monolithic substrate opposite to the first face.

The term "communication system" is intended to have its ordinary meaning in the art. In various embodiments, the communication system can comprise a single component or a plurality of components in order to transmit information from the sensor circuit to an external device. For example in various embodiments according to the present disclosure the communication system may comprise an LED, a laser, or an RF antenna. In embodiments the communication system may transmit a signal in corresponding to the current outputted by the sensor circuit. In alternative embodiments of the present disclosure the communication system can take more complex forms. For example the communication system may comprise a modulator, an output driver, and a transmission system. The communication system may additionally comprise a pulse code modulator which can be used to modulate the transmitted signal.

A "monolithic substrate" is a substrate, upon which components are monolithically integrated and therefore such components are not adhered and/or secured via mechanical means to the substrate. In various embodiments according to the present disclosure the monolithic substrate can be the result of processing using CMOS technology or other fabrication technology known to the skilled person. It is understood that a monolithic substrate has multiple faces, and at least a first face and a second face. A first and second face can be distinguished from other faces of the monolithic substrate in that the first and second face are larger than the other faces of the monolithic substrate.

The term "sensor" refers to the region of the device responsible for the detection of a particular biological indicator. For example, in some embodiments for glucose monitoring, the sensor interface refers to that region wherein a biological sample (e.g., blood or interstitial fluid) or portions thereof contacts an enzyme (e.g. glucose oxidase); a reaction of the biological sample (or portion thereof) results in the formation of reaction products that allow a determination of the glucose level in the biological sample. In various embodiments of the present invention, the sensor further comprises a "functionalization layer" as described later in the present disclosure. In various embodiments of present disclosure the sensor can be monolithically integrated into the monolithic substrate. In various embodiments of the present disclosure the monolithically integrated sensor can be placed on a different face of the monolithic substrate from the power supply. This can be done in various embodiments by forming for example high surface electrodes similarly to the method described below on a silicon face of the monolithic substrate and interconnecting them through the monolithic substrate to the other face of the monolithic substrate comprising the power supply.

The term "power supply" is intended to have its ordinary meaning in the art. In various embodiments according to the present disclosure the power supply can comprise an RF antenna or photovoltaic cell for receiving external energy.

Various embodiments according to the present disclosure may be of different sizes. In various embodiments the device will be less than 1 mm long and 1 mm wide with a height of less than 200 microns. In various other embodiments the device will have a height of less than or equal to 200 or 100 microns and a length and a width of less than or equal to 500 microns.

In various embodiments the device according to the present disclosure may comprise a sensor circuit. The sensor circuit can comprise a circuit that processes signal from the sensor into a form easily conveyed by the communication system. In various embodiments the sensor circuit may consist of a potentiostat. In alternative embodiments the sensor circuit 102 may comprise a potentiostat 107 and a current mirror 108 as seen in FIG. 1.

A modulator as understood in the present disclosure indicates a circuit that varies one or more properties of a periodic waveform in response to variations in an input of the modulator provided by the sensor circuit (e.g. modulation signal). In various embodiments according to the present disclosure the modulator can comprise a pulse-width modulator 104 that increases the width of a pulse sent from the device (e.g. to the input of the modulator) depending on an output (e.g. current output) of the sensor circuit 102.

Various embodiments of the present disclosure comprise an output driver. In some embodiments according to the present disclosure an output driver can increase a current provided by the modulator output such as to allow transmission at an acceptable power level of the modulator output by the transmission system of the implantable device. In various embodiments the output driver 105 may comprise one or more transistors possibly handling a large current that increases the current provided by the pulse width modulator 104.

A transmission system in the as described through the present disclosure may comprise a laser (e.g. VCSEL), LED, RF antenna.

The term "potentiostat," is used herein, in its ordinary sense, including, without limitation, an electrical system that controls the potential between the working and reference electrodes of at least a three electrode cell at a present value. It controls a current that flows between the working and counter electrodes to keep the desired potential, as long as the needed cell voltage and current do not exceed the operational limits of the potentiostat.

Figure 2:
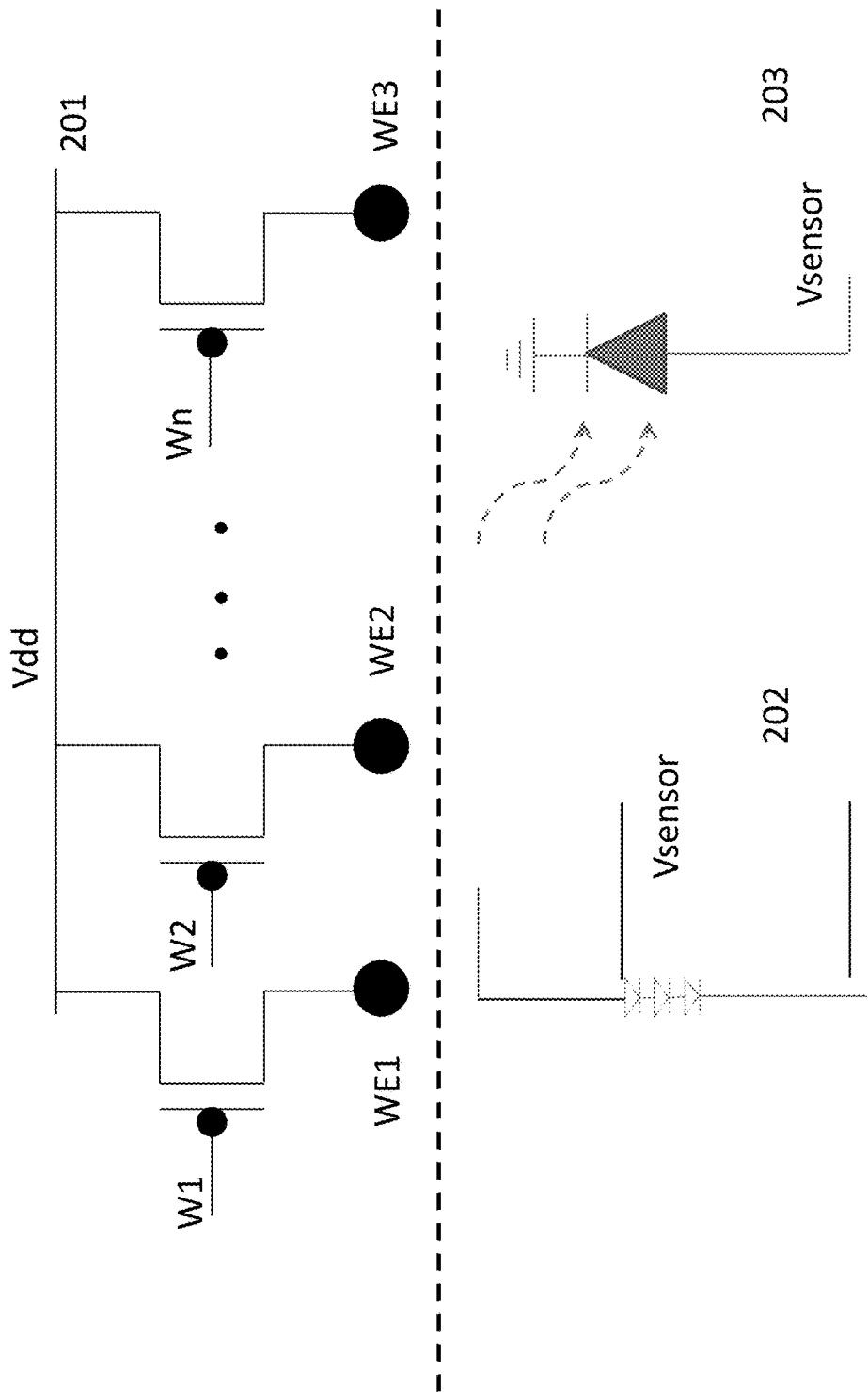
FIG. 2 illustrates an exemplary embodiment of multiple working electrode (WE) switching circuitries and Vsensor current input means.

An example of a potentiostat circuit 107 is seen in FIG. 1. The potentiostat 107 includes electrical connections to a working electrode (WE), reference electrode (RE), and a counter electrode (CE). In various embodiments according to the present disclosure multiple working electrodes (WE) could be used via transistor switching as seen in FIG. 2. In FIG. 2 transistor switching is used to switch between n working electrodes (e.g. WE1, WE2, WEn) via opening or closing switches W1, W2, Wn by an isolated voltage provided to each switch (W1, W2, Wn). In various embodiments the switching voltage to open transistor switches W1, W2, and Wn may come from an external source (e.g. photovoltaic). The voltage applied to the working electrode WE and the voltage applied to the reference electrode RE are set such that the voltage difference applied between the working electrode WE and reference electrodes RE is maintained at a constant value or swept between values (e.g. voltages). The counter electrode CE is configured to have a current equal to the amount measured by the working electrode WE by varying the voltage at the counter electrode CE to balance the current going through the working electrode WE such that the current does not pass through the reference electrode RE. This can be accomplished by an OP AMP 110 with a negative feedback loop connected to both the reference electrode RE and counter electrode CE. The input current for the OP AMP 110 Vsensor can in various embodiments according to the present disclosure from be generated from the power supply itself 202 or an independent photodiode 203 as seen in FIG. 2.

A current mirror is a circuit well known by a person skilled in the art and which is used to control a current output independent to a loading presented to the circuit. An example of a current minor can be seen in FIG. 1 at 108. The current mirror in this exemplary embodiment replicates the sensor current from the potentiostat 107 without actually loading the potentiostat 107 thereby isolating its performance. In this exemplary embodiment depicted in FIG. 1 of the present disclosure the current from the potentiostat 107 ("Isensor") is mirrored by the current mirror 108 via matching transistors.

A control circuit can control energizing of the various components of the implantable device. In various embodiments of the present disclosure a control circuit 103 can be present such as to control operation of the device while in alternative embodiments the current from the sensor mirror 108 can flow directly into the pulse width modulator 104. In one embodiment of the present disclosure the control circuit 103 receives a current from the current mirror 108 and the control line (control). A current into the transistor of the control circuit 103 from the control line enables the current from the current mirror 108 to enter the pulse width modulator 104, input driver 105, and transmission system 106. The control circuit 103 serves as a switch which when enabled via the control line "control", enables operation of the modulator and thereby transmission of data by the device. The control line can be connected to an oscillator as seen at 301 of FIG. 3A or a photovoltaic cell as seen at 302 of FIG. 3A. The timing of the oscillator 301 can be controlled by the relative ratios of the transistor sets (e.g. x and y). The oscillator 301 can result in voltage to the control line (control) at short regular intervals relative to intervals as seen in the graph of FIG. 3B. In various embodiments, the photovoltaic cell at 302 can be activated by a different wavelength than that of the power supply or other photovoltaic cells on the implantable device thereby providing control over the activation of the pulse-width modulator 104 and the input driver 105 and transmitter system 106. By limiting an ON time of the pulse-width modulator 104, input driver 105, and transmitter system 106 the implantable device can limit the amount of heat generated by the device. The temperature is limited by limiting the power transmitted by the transmitter system 106 under control of the control circuit (when present). The temperature is limited because minimal heat is generated by the pulse width 104 modulator and output driver 105 because said systems are at some time periods not activated.

A pulse width modulator can comprise various circuits to transform the current from the current mirror 108 and control circuit 103 into a series of pulses. According to one embodiment of the present disclosure, depending of the current from the current mirror 108 and the control circuit 103, the pulse width modulator 104 varies the width of the pulses generated via an internal oscillator 109. The pulse width modulator 104 then feeds the pulses into the input driver 105 and transmission system 106. It should be noted that under control of the "control" signal, the control circuit, during an active portion of the device, provides current from the sensor circuit (e.g. current mirror) to the lower section of the modulator (104) and therefore enables operation of the modulator as enabling the lower section can allow a current flow from the top section to the lower section of the modulator (104).

Figure 4:
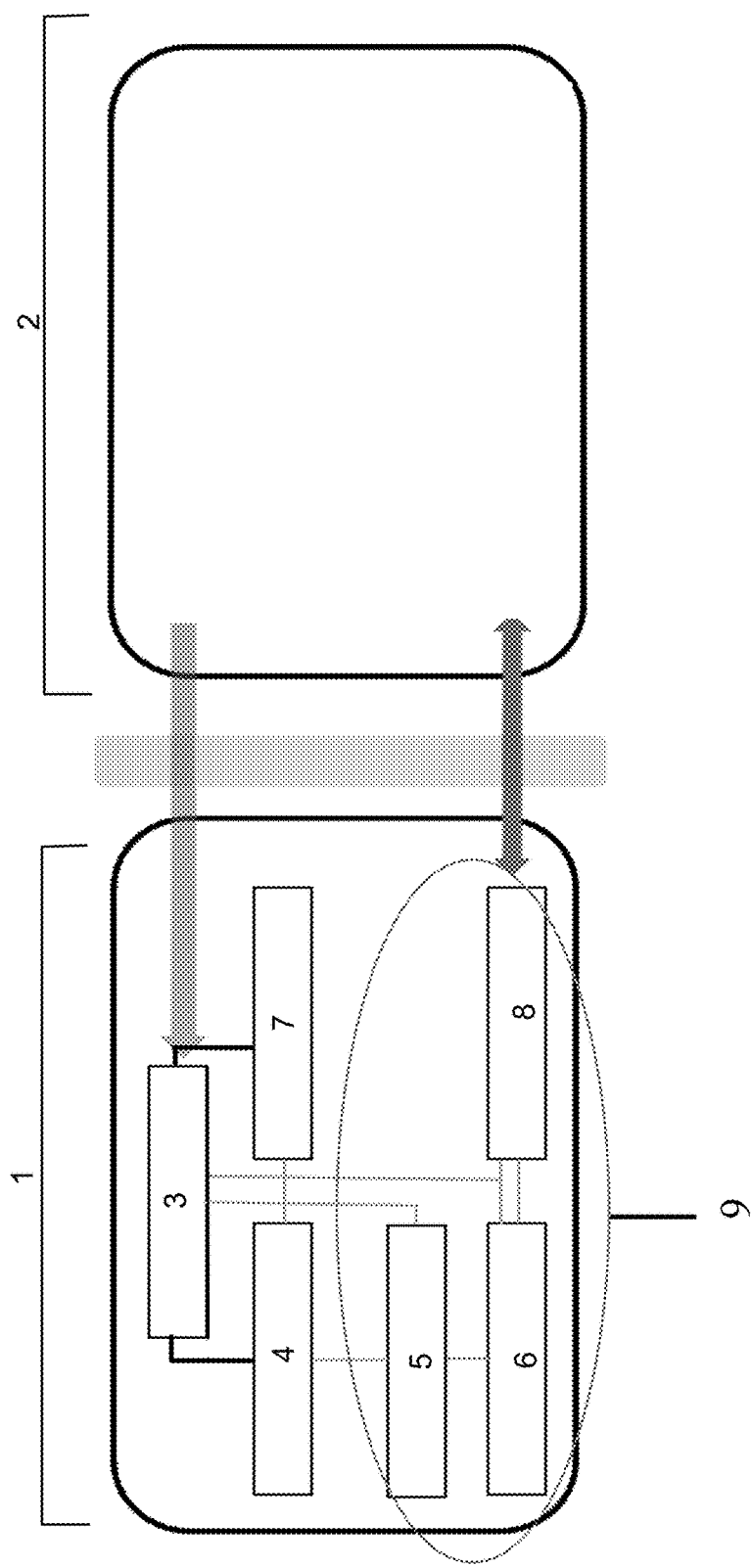
FIG. 4 illustrates an exemplary block diagram of the implantable device.

The function and interrelationship of the communication system 9, sensor 7, power supply 3, and sensor circuit 4 is illustrated in an exemplary embodiment of the present disclosure of FIG. 4 of the present disclosure. In this embodiment, the power supply 3 is operably connected to the communication system 9, sensor circuit 4 and sensor 7. The communication system 9 receives a processed signal from the sensor circuit 4 which is operably connected to the sensor 7.

In an exemplary embodiment according to the present disclosure the communication system 9 comprises a modulator 5, output driver 6, and transmission system 8. In such an embodiment the power supply 3 is operably connected to the modulator 5, output driver 6, transmission system 8, sensor circuit 4, and sensor 7. The sensor circuit 7 is operably connected to the modulator 5 that modulates the information from the sensor circuit 4. The information is sent to the output driver 6 where a corresponding power of the modulated information is increased and subsequently fed to the transmission system 8 of the implanted device for transmission.

A working electrode is an electrode in an electrochemical system on which a reaction of interest is occurring. The working electrode is often used in conjunction with a counter-electrode, and a reference electrode in a three electrode system. Common working electrodes can consist of noble metals such as gold, silver, and platinum. Exemplary working electrode in the subject invention further includes high surface area electrodes.

A reference electrode is an electrode which has a stable and well-known electrode potential. Example reference electrodes include electrodes made with inert metals such as gold, silver, platinum and silver/silver chloride.

A counter electrode is an electrode commonly used in a three-electrode system for voltammetric analysis. In a three-electrode cell, the counter electrode can be used to provide a circuit over which current is either applied or measured. The potential of the counter electrode is usually not measured and can be adjusted so as to balance the reaction at the working electrode. A counter electrode in various embodiments can be fabricated from a variety of chemically inert materials such as gold, platinum, or carbon.

In various embodiments the implantable device can comprise 1, 2, 3, 4 or more working electrodes as previously discussed in the present disclosure in connection to FIG. 2. In glucose sensing, embodiments glucose oxidase is used to produce hydrogen peroxide from glucose and thereby the oxygen to drive the sensor; however, glucose oxidase can degrade from a variety of mechanisms when implanted within the body such as thermal and chemical denaturing as well as protease degradation. It follows that according to further embodiments of the present disclosure, a novel protected working electrode is presented which can increase the total longevity of implantable devices according to the present disclosure can be increased.

In various embodiments at least one electrode can be coated with a biodegradable polymer as to protect the electrodes for a time frame. Biodegradable polymers are non-toxic, capable of good mechanical integrity until degraded, as well as capable of a controlled rate of degradation. Examples of suitable biodegradable polymers include polyglycolide (PGA), polylactide (PLA), and polycaprolactone (PCL). Said polymers can be applied to the device by pipetting onto the portion of the device displaying the electrode.

A photovoltaic power supply is a power supply that creates electrical current upon exposure to light which can be related to the photoelectric effect. When light is incident upon a material surface, the electrons present in the valence band absorb energy and, being excited, jump to the conduction band and become free. These highly excited, non-thermal electrons diffuse, and some reach a junction where they are accelerated into a different material by a built-in potential. This generates an electromotive force, and thus some of the light energy is converted into electric energy. An example of a photovoltaic power supply implementable on a monolithic substrate would include for example a p-n junction solar cell.

A CMOS die is a die that is designed for CMOS processing. Examples of commercially available CMOS include dies from TSMC 250 nm and IBM 250 nm. The skilled person will know of other technologies and processes which can be used for monolithic integration.

Figure 5:
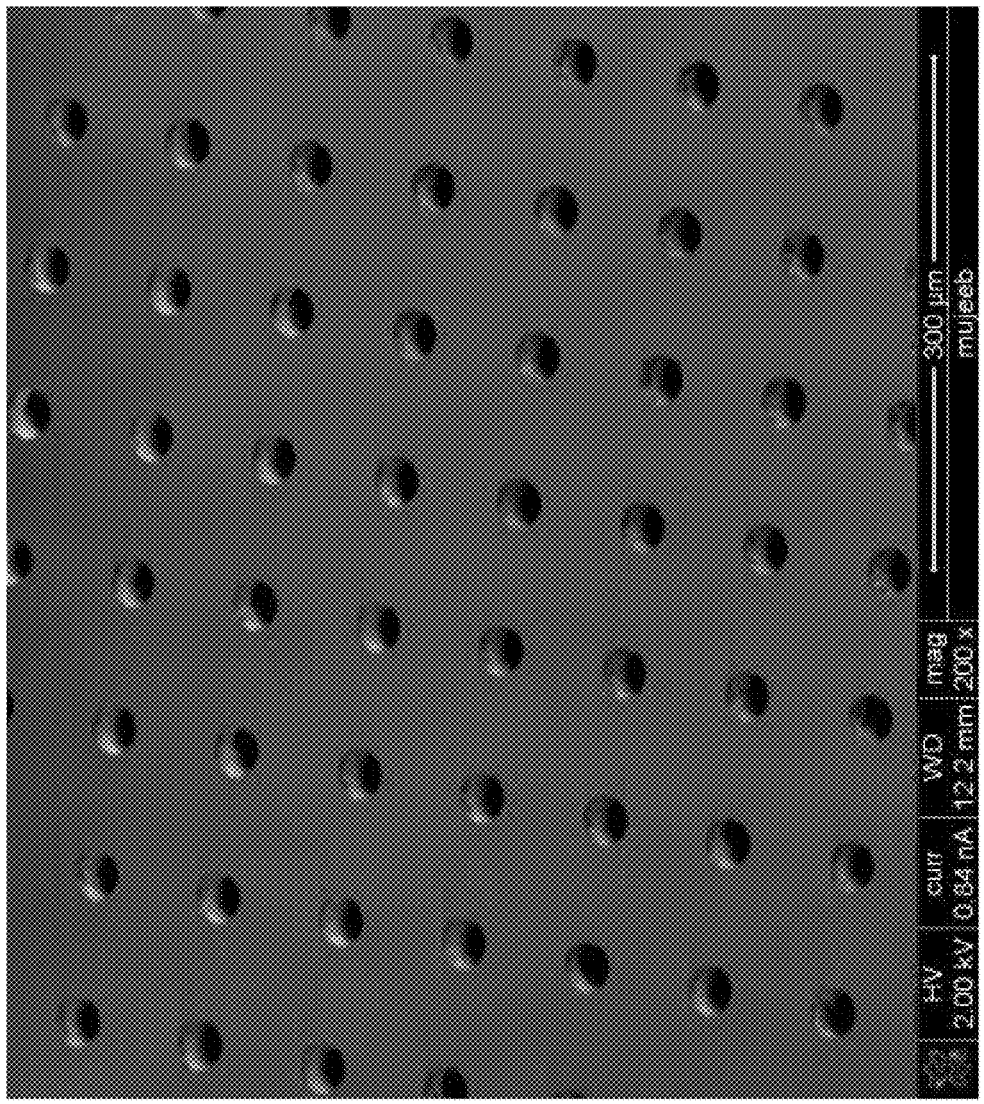
FIG. 5 shows holes formed into a monolithic substrate.

Various embodiments comprise a hole that passes from a first side of the monolithic substrate to a second side of the monolithic substrate. Holes can be made using a variety of different methods. UV laser ablation can be used to make holes as corresponding wavelengths can ablate both dielectrics and silicon layer. Gas based etching can also be used. Pseudo-Bosch process is an example of plasma processing. Holes resulting from a pseudo-bosch process can be seen in FIG. 5 of 30 micron size.

In various embodiments a hole 607 or holes can be used to allow implantable device to be secured to bone or various other tissues via a metal, fiber or polymer based insert that fits into the hole. In various embodiments the hole or holes can be located in different regions of the substrate. In various embodiments 1, 2, 3, 4, or more holes can be provided.

In various embodiments, holes can allow liquid to pass through the device. Holes by allowing liquid to pass through the device may minimize foreign body capsule and in various instances may prevent clogging of the circulatory system by allowing passage of circulatory fluid even if the device becomes lodged in a circulatory vessel.

An interconnect may links two regions of the implantable device, such as, for maybe, different faces of the implantable device. Herein interconnects 608 of FIG. 6 can be conductive material such as copper that can connect to different components or provide connections within components on the monolithic substrate 601.

Figure 6:
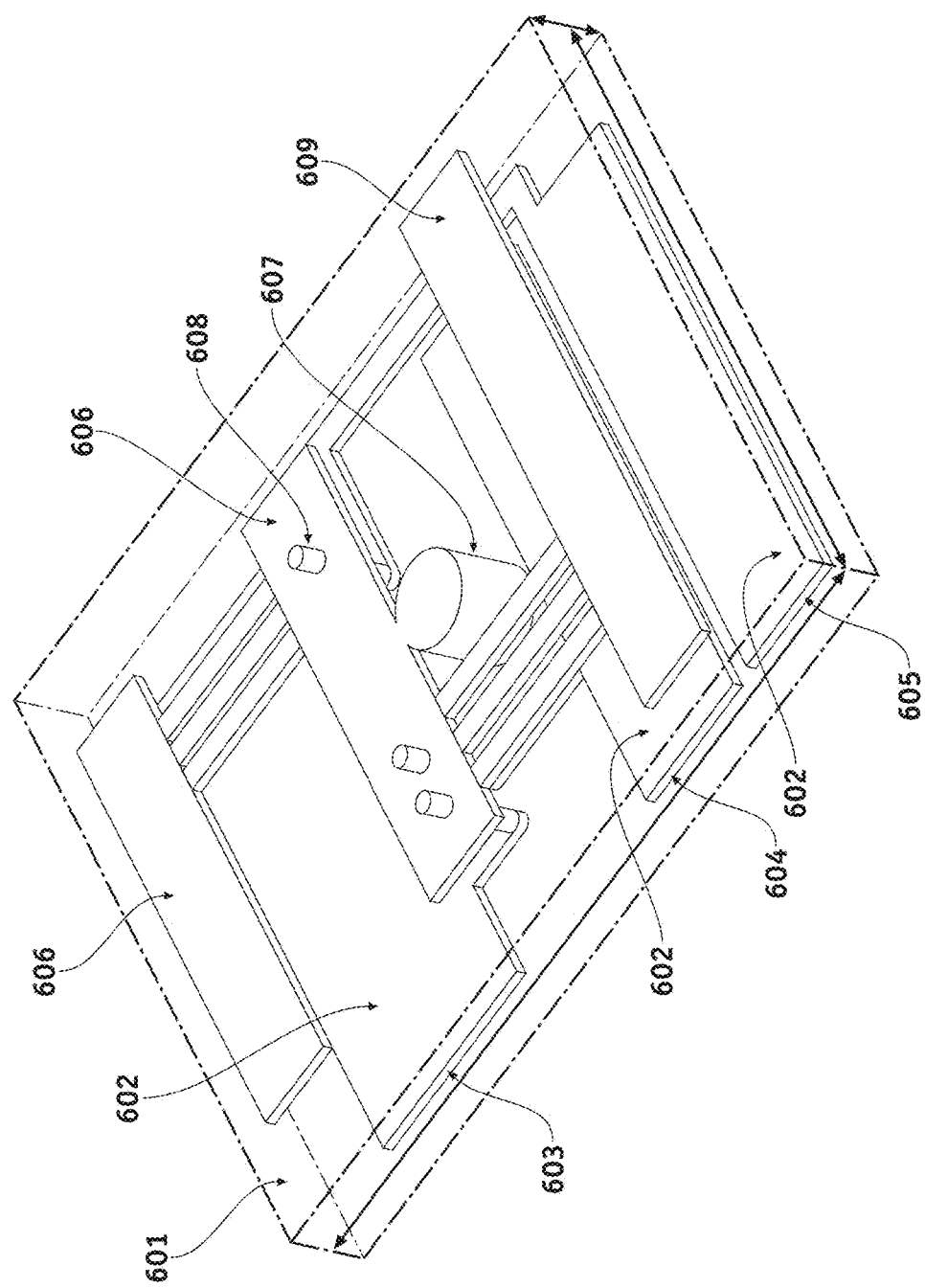
FIG. 6 illustrates an exemplary embodiment of the configuration of the implantable device.

An exemplary interrelationship of a communication system and sensor circuit 606, sensor 602, power supply 609 can be seen in FIG. 6. In FIG. 6 the communication system 606 is on first face the monolithic substrate 601 and the sensor 602 is located on a second face of the monolithic substrate 601. In FIG. 6 the sensor comprises 3 electrodes: a single counter-electrode 603, a single reference electrode 604 and a single working electrode 605. In FIG. 6 the monolithic substrate 601 comprises a hole 607. The sensor 602 is connected to the communication system and sensor circuit 606 via interconnects that electronically link a first face of the monolithic substrate with a second face of the monolithic substrate.

High surface area electrodes can mean an electrode with a surface area exceeding the classic dimensions of its surface. Further disclosure related to high surface area electrodes can be found in U.S. application Ser. No. 14/106, 701, filed on Dec. 13, 2013, herein incorporated by reference in its entirety. In various embodiments according to the present disclosure the high surface area can be formed by pillars.

In exemplary embodiments according to the present disclosure the design of the pillars can be made using commercial software. PMMA 950 A4 can be used to achieve clean lift-off while still achieving a desired resolution. The resist can be spun at 4000 rpm for 1 minute followed by a 180° C. bake for 5 minutes. A dose of 1200 μc/cm$^2$ can be used to write the pattern in a Leica EBPG5000+ optical system. Patterns can be developed in 1:3 solution of MIBK and IPA for 20 seconds followed by a deionized water rinse. Afterwards, a 50 nm alumina mask can be sputter coated in a Temescal TES BJD-1800 DC reactive sputter system by depositing aluminum in oxygen plasma for 5 minutes. Lastly, mask liftoff can be performed in dicholoromethane in an ultrasonic bath for 2 minutes. Successful patterning was confirmed by optical microscopy (not shown).

Figure 7:
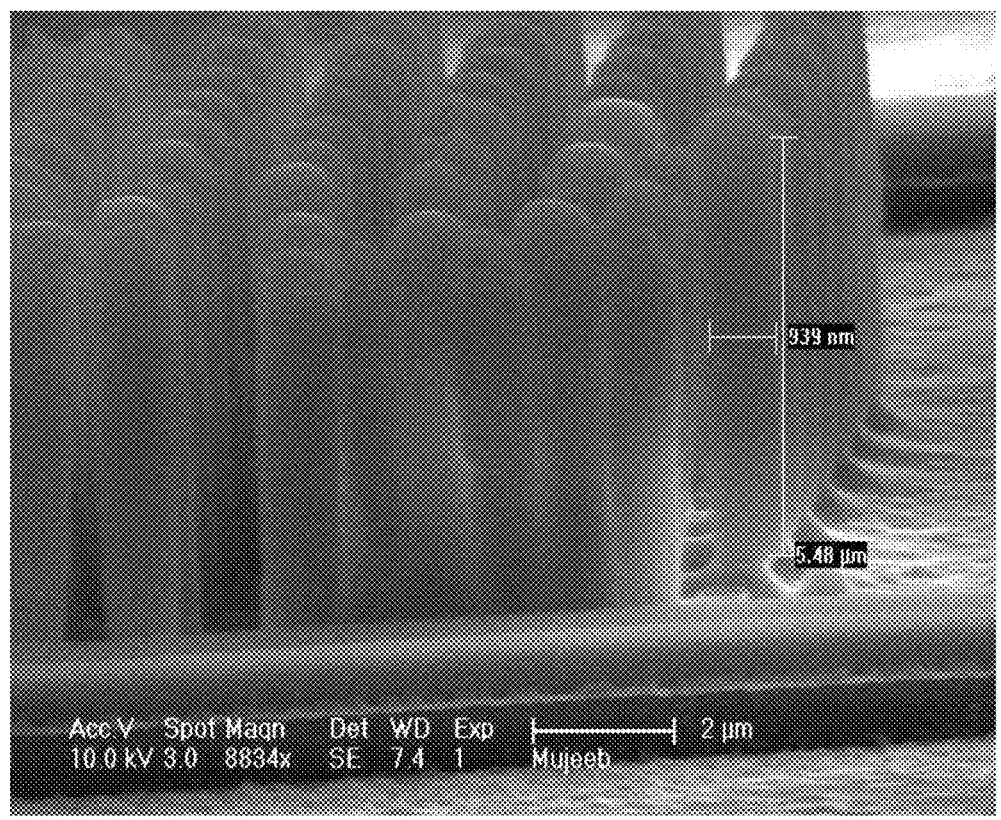
FIG. 7 shows the formation of pillars on CMOS.

In exemplary embodiments according to the present disclosure patterning can next be performed with a MA-N 2403 resist. Pillars were fabricated using both dry plasma ($Cl_2$: $BCl_3$) as well as wet etchants (e.g. TMAH) to etch away parts of the metal pad using a UNAXIS RIE machine. For the dry plasma ($Cl_2$:$BCl_3$) etch, the temperature was set to 25 degrees Celsius and RIE power to 120 watts. Flow rate for $Cl_2$ was set to 4 SCCM and the flow rate of $BCl_3$ was set to 20 SCCM. For the wet TMAH etch the surface can be submerged in a liquid for room temperature for 10 minutes. A resulting exemplary embodiment according to the present disclosure using the above procedure can be seen in FIG. 7. Success can be seen in the dimensions and uniformity of the formed structure.

Figure 8:
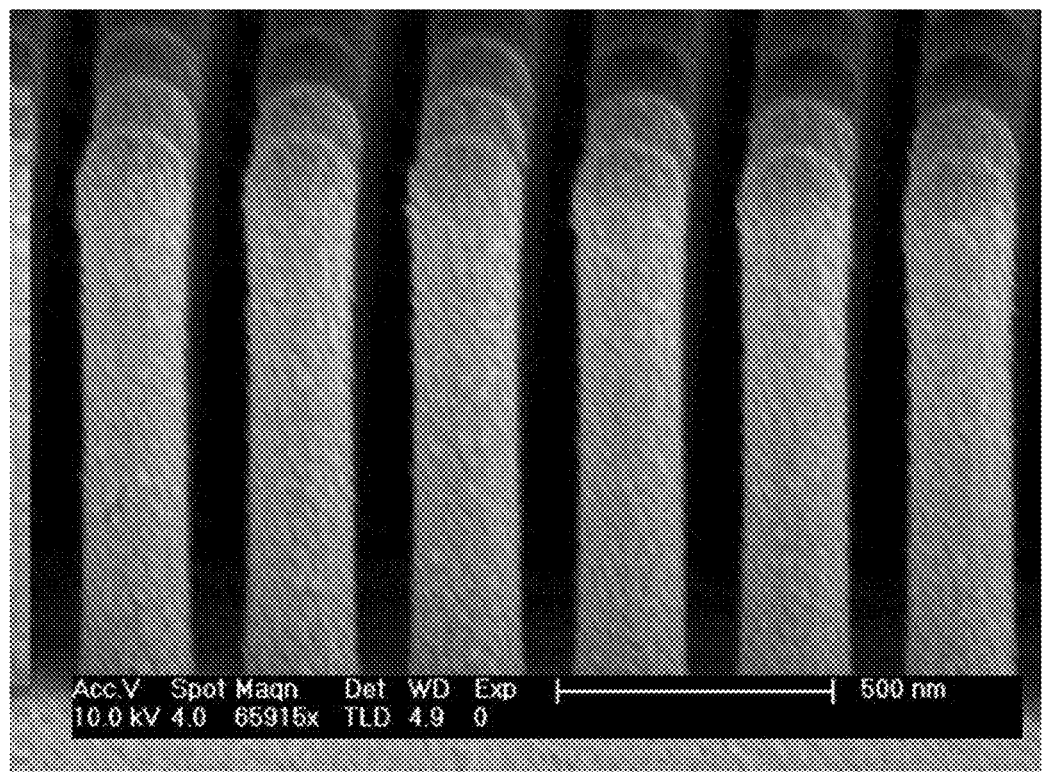
FIG. 8 and FIG. 9 show the coating of pillars.
Figure 9:
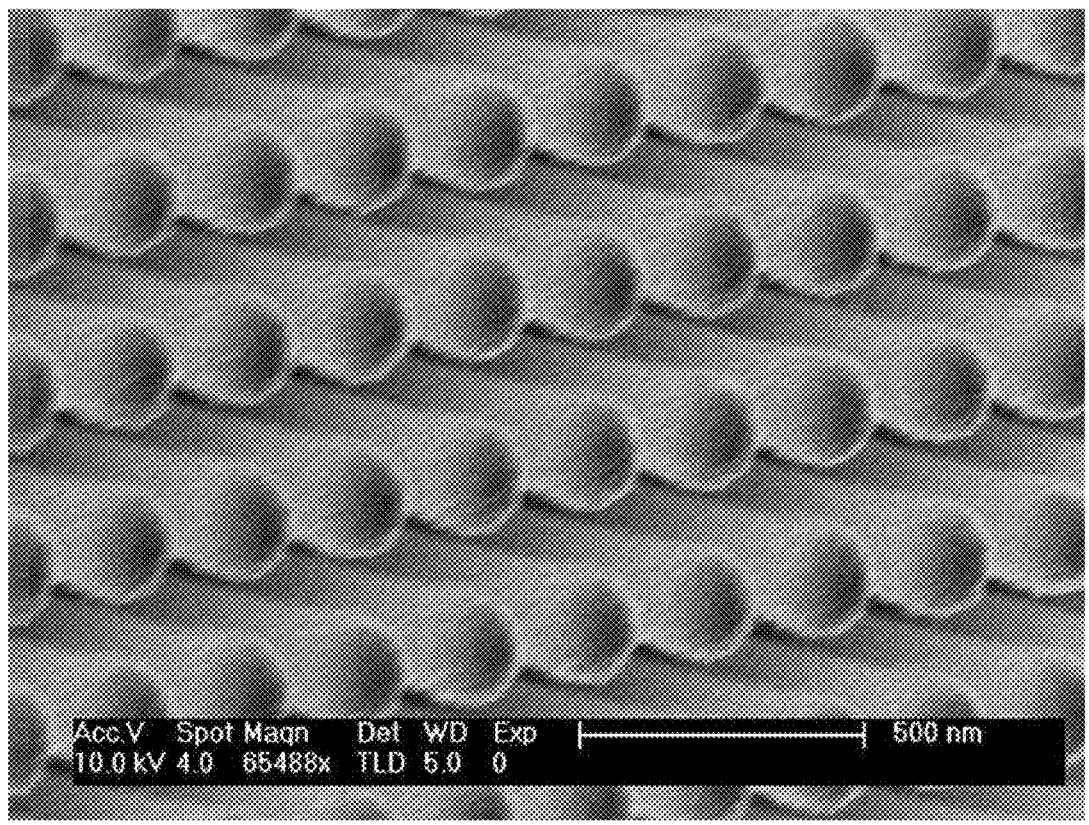

In exemplary embodiments according to the present disclosure, metal deposition sputtering can be used to perform conformal coatings. First high density Argon plasma of 20 mTorr is used to increase the isotropy of the deposition. A 5 nm Ti adhesion layer is DC sputtered and then 50 nm or 100 nm Au or Pt films were DC sputtered. Resulting embodiments according to the present disclosure using the above procedure can be seen in FIGS. 8-9. A special stage was used which could tilt the sample with respect to the incoming metal atoms at angles up to 90° C. Secondly, the stage could rotate at speeds up to 120 r.p.m. A combination of tilt and rotation along with optimization of plasma parameters (high pressure, around 20 mTorr) resulted in very uniformly controlled conformal sidewalls.

A material substantially covering all the device except for the electrode and laser can be accomplished by a variety of techniques in the art and in a variety of geometries. In various embodiments SU8, Parylene, PDMS, or Silicone are used. Parylene is applied using vacuum deposition.

Figure 10:
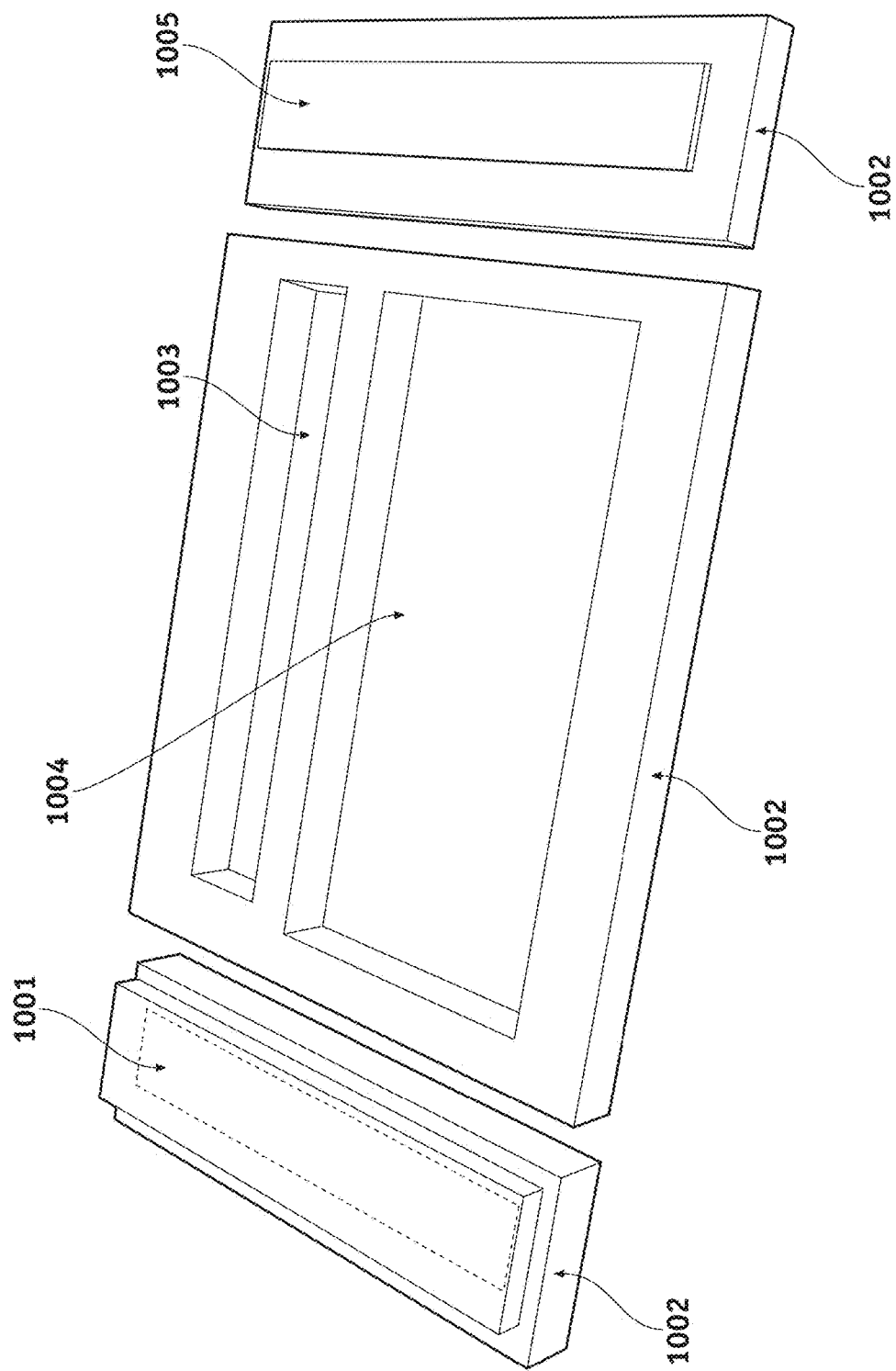
FIG. 10 illustrates the material coating of the monolithic substrate.

FIG. 10 shows embodiments of the implantable device with a material 1002 for protecting the "functional layer" (1001 and 1005) of the electrodes. In this exemplary embodiment the material 1002 surrounds both a first functional working electrode (beneath 1005) and a second function working electrode (beneath 1001). Wells have also been formed by the material 1002 for the counter-electrode 1004 and the reference electrode 1003. The well can be shaped differently to correspond to different electrode configurations. In various embodiments the material covers the implantable device except for the electrodes thereby supporting the functionalization matrix (not shown). In various embodiments the material substantially covers the implantable device except for the electrodes and transmission system (not shown).

In one exemplary embodiment according to the present disclosure to substantially cover a material comprising a compatible polymer, SU8 can be applied to the entire surface of the device by spinning at 2000 rpm for 1 minute followed by a bake at 95° C. for 5 minutes. Next a dose of U.V. light at 365 nm can be used to write a pattern corresponding to the electrodes in a Carl Suss mask aligner system for 6 seconds. After expose the device can again be baked at 95° C. for 5 minutes. Patterns can be developed in SU8 developer solution for 5 minutes followed by a water rinse.

In various embodiments the electrodes are covered by a "functional layer" to provide specificity to a target of interest. The phrase "functional layer" refers to a layer comprising any mechanism (e.g., enzymatic or non-enzymatic) by which a target of interest can be detected into an electronic signal for the device. For example, some embodiments of the present invention utilize a functional layer containing a gel of glucose oxidase that catalyzes the conversion of glucose to gluconate: Glucose+$O_2$→Gluconate+$H_2O_2$. Because for each glucose molecule converted to gluconate, there is a proportional change in the co-reactant $O_2$ and the product $H_2O_2$, one can monitor the current change in either the co-reactant or the product to determine glucose concentration. In various embodiments of the present disclosure the functional layer can comprise a hydrogel (e.g. BSA) loaded with an enzyme (e.g. glucose oxidase). In various alternative embodiments of the present disclosure the functional layer can also be a polymer (e.g. polypyridine) loaded with an enzyme (e.g. glucose oxidase).

In various embodiments according to the present disclosure the counter electrode can be an order of magnitude larger or more than the working electrode. The counter electrode can be larger in order to not limit the working electrode in any way and hence not limit the cell impedance. In various embodiments the potential across the working and counter electrode is pulsed. The working electrode and the counter electrode of implantable device require oxygen in some embodiments when detecting glucose. Within the functionalization layer above the electrode oxygen is required for the production of hydrogen peroxide from glucose. The hydrogen peroxide produced from the glucose oxidase reaction further reacts at the surface of the working electrode and produces two electrons. The products of this reaction are two protons ($2H^+$), two electrons ($2e^-$), and one oxygen molecule ($O_2$). The oxygen concentration near the working electrode, which is consumed during the glucose oxidase reaction, is replenished by the second reaction at the working electrode; therefore, the net consumption of oxygen is zero. The counter electrode uses oxygen as an electron acceptor. The most likely reducible species for this system are oxygen or enzyme generated peroxidase. There are two main pathways by which oxygen may be consumed at the counter electrode. These are a four-electron pathway to produce hydroxide and a two electron pathway to produce hydrogen peroxide. Oxygen is further consumed above the counter electrode by the glucose oxidase.

Figure 11:
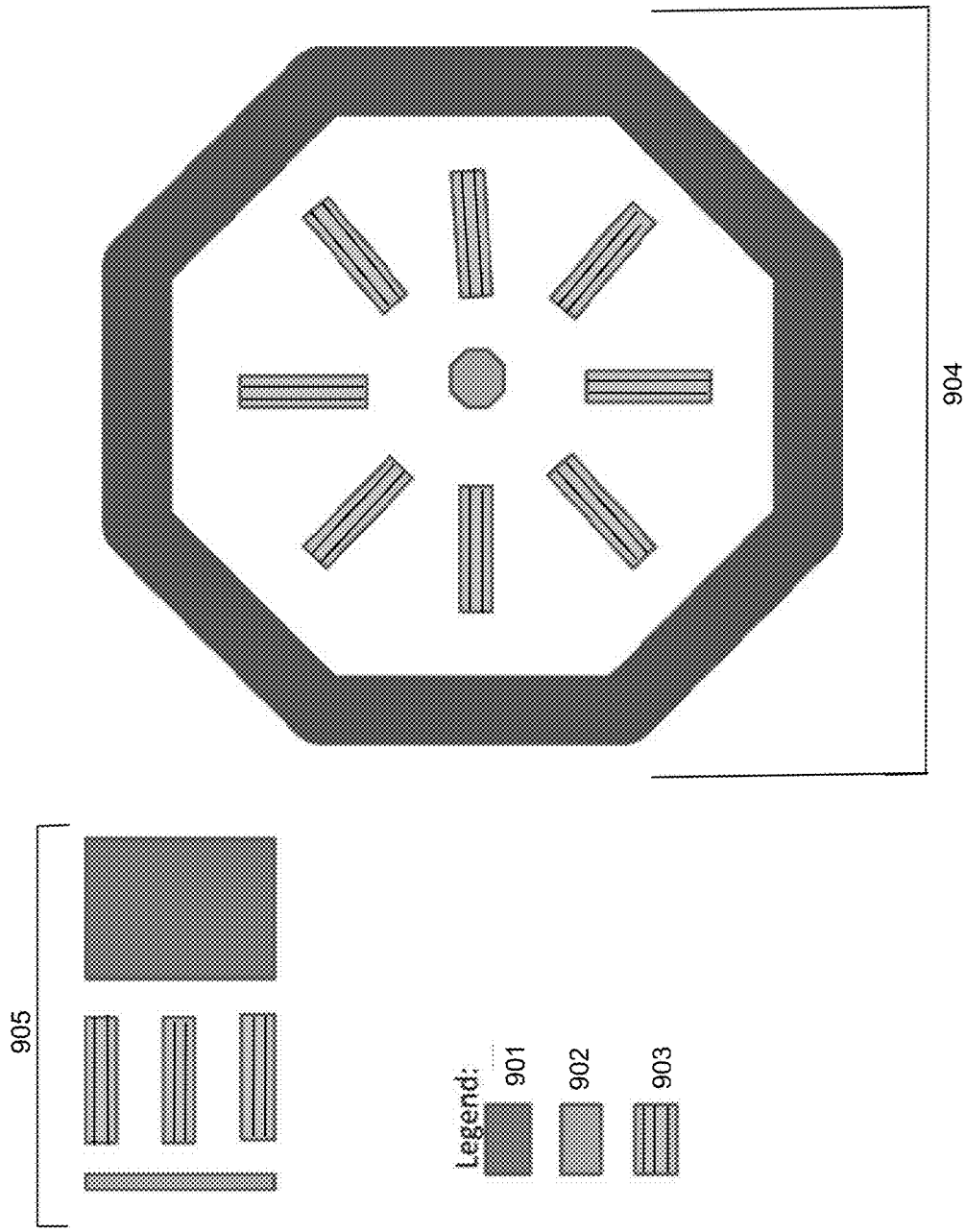
FIG. 11 illustrates various geometries possible for multiple counter electrode (CE), reference electrode (RE), and working electrodes (WE).

In various embodiments the working electrodes of the device can be laid with varying degrees of symmetry. FIG. 11 shows embodiments with multiple working electrodes (WE). In configuration 905 three working electrodes (903) are arranged equally distant from the counter electrode 901 and reference electrode 902. In configuration 904 eight working electrodes (903) are arranged inside an octagonal counter electrode 901 with each working electrode (903) equally distant from an equivalent surface distance of the reference electrode 902 and the counter electrode 801. Configurations such as 904 where each working electrode 903 appears spatially similar to alternative working electrodes 903 may minimize the need of recalibration. Recalibration may be needed in different geometries if the spacing difference of the electrodes may affect performance of the reaction. Additionally, the use of such a symmetric configuration as depicted in FIG. 11 may allow use of same electronics as the implantable device switches from one working electrode to a different working electrode. Such switching may depend on various needs such as glucose oxidase degradation and exposure of alternative electrodes by biodegradable coating degradation.

An embodiment of the present disclosure comprises a method for operating an implantable device comprising receiving power for first interval of time at the implantable device and transmitting information for a second interval of time from the implantable device.

Power received by the implantable device in various embodiments can comprise forms such as electromagnetic (light), mechanical, thermal, vibrational (sound waves), or electrical. In an exemplary embodiment the power is optical (e.g. near infrared, 700 to 1000 nm).

An interval of time for receiving power (e.g. by the implantable device) in various embodiments can span from microseconds to tens of seconds, greater than about 0.1 seconds but less than about 5 seconds, or greater than about 0.5 seconds but less than about 2 seconds. In embodiments of the implantable device wherein the implantable device comprises at least a modulator, the interval of time for receiving power can exceed a millisecond.

Transmitting information (e.g. information corresponding to the sensed signal of the implantable device, information corresponding to the level of glucose) for an interval of time can comprise transmitting information for a period spanning from microseconds to tens of seconds, an interval of time of greater than about 0.1 seconds but less than about 5 seconds, or an interval of time greater than about 0.5 seconds but less than about 2 seconds.

In various embodiments according to the present disclosure the first interval of time can substantially equal the second interval of time. Such a configuration can be seen when the potentiostat 107 is directly connected to the output driver 105 and hence the transmission system 106. In various embodiments according to the present disclosure the second interval of time can be contained within the first interval of time.

Figure 12:
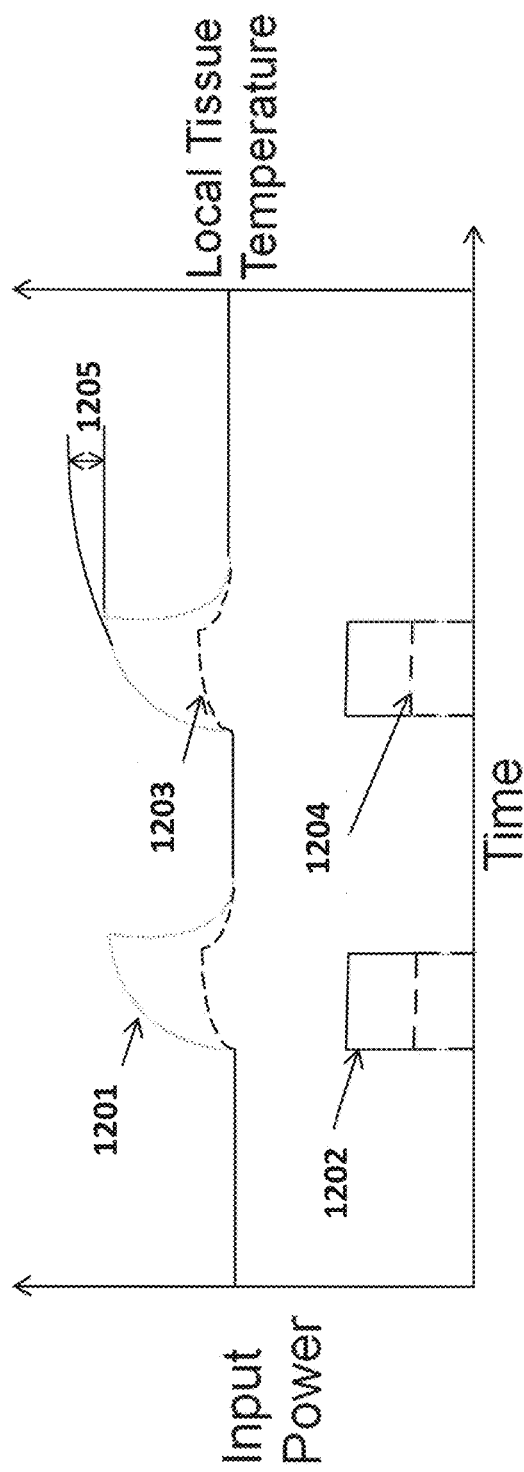
FIG. 12 shows the effect of pulsed energy on tissue temperature using both RF and optical energy.

Any electronic device has a minimum amount of power needed to drive the circuitry of the device and continuously providing said power to an implantable device can result in a high temperature in the local region surrounding the implantable device. A high temperature in tissue of a living body can result in damage to the tissue. A potential solution according to the present disclosure devised to avoid a high temperature can be to receive power only for certain intervals and transmitting information for only certain intervals or in alternative embodiments of the present disclosure sub intervals of the intervals. Time versus power with RF and optical power pulses was calculated. The results are seen in FIG. 12. In FIG. 12 it can be seen that during a pulse of energy (1202, 1204) a device can receive an amount of power without reaching the steady state temperature associated with continuous powering of device (see 1201 and 1203). The difference between the steady state temperature associated with a given amount of energy and that found when the power is pulsed can be seen at 1205. Hence various embodiments of the present disclosure can relate to powering and transmitting information in short pulses thereby maximizing the difference in temperature between the steady state and pulsed operation while permitting powering of the implantable device and while delivering enough information to understand the status of the reaction monitored by the sensor (i.e. the concentration of glucose).

The use of such short pulses may go against common practice as often devices require an extended period of time to completely stabilize (e.g. the wavelength of some lasers may vary before reaching steady state after continuous powering). This variance associated in operating temperature of the device from a steady state temperature with shorter powering can be undesirable in medical applications where performance is critical before realizing the temperature advantages of the present disclosure.

Powering the device for only an interval of time corresponding to a period of time the power is received means that the device at times when no power is received is powered down and thereby at a steady state corresponding to a received background power (e.g. from background light).

In various embodiments, a fraction of a second can be sufficient for an optical readout according the present invention to capture data to an external device. Such embodiments can, for example, be obtained when the system is designed for pulse communication schemes. For example, for electrochemical waveforms for biological sensing, the fastest scan rates (e.g. for cyclic Voltamograms or Chronoamperometric measurements) are few Hz at most. Hence, a system designed to operate at KHz can easily capture (send/receive) this data in real-time. The same can be true for RF and acoustic methods used to detect such slowly changing signal.

In various embodiments, the pulse intervals can be used in actively transmitting systems or a passive communication scheme where a focused input beam is modulated by the communication system.

In various embodiments, the receiving a signal separate from the receiving power to initiate the transmitting of information for an interval of time can allow the power source to power the device and then can allow a separate signal from an external device to control information flow when desired from the internal device (e.g. allows the external device to set a time period after powering the device until the transmittal of the blood glucose level).

In various embodiments, the power received is at a different wavelength than the wavelength of the power transmitted. This reduces interference of the transmitted signal and allows wavelength-based filtering at an external device.

An embodiment of the present disclosure comprises a system comprising an implantable device as described above and an external device including a processor connected to a power transmitter and a power source, the processor configured to activate the power transmitter only for certain intervals.

In various embodiments the external device can comprise a power source 1501, processor 1502, detector 1503, transmitter 1506, display 1504, and communication link 1505. In various embodiments these components can further comprise various components (e.g. power source 1501 comprising a solar cell 1510, a power management chip 1511, and a battery 1512). In various embodiments the external device can comprise additional components such as a push switch 1507, buzzer 1508, and/or touch sensor 1509.

Figure 16:
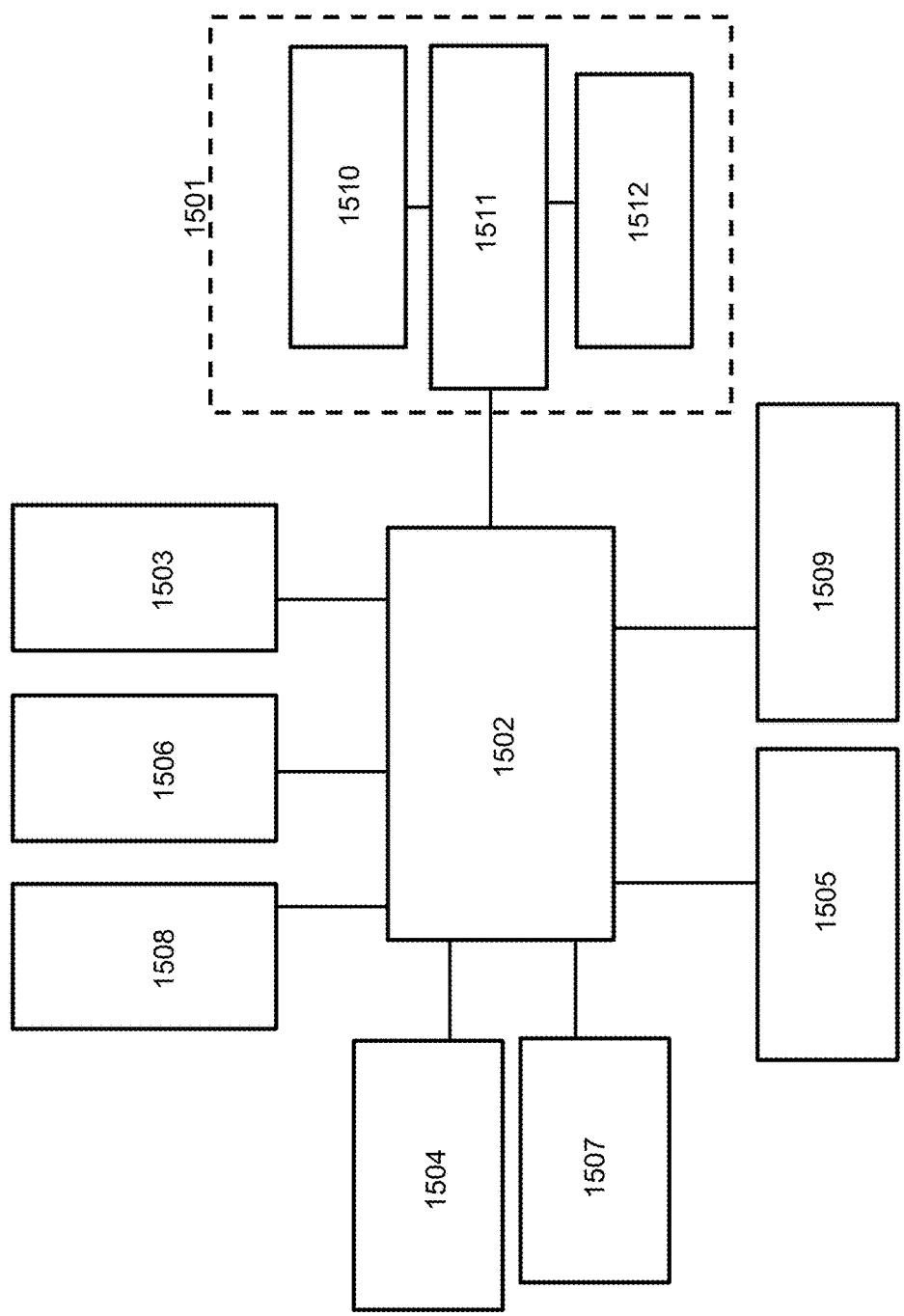
FIG. 16 shows an exemplary block diagram of the external device.

A processor 1502 is a component that carriers out instructions of a computer program by performing the basic arithmetic, logical, and input/output operations of the system. In various embodiments, the processor can be a microprocessor that incorporates all the functions on a single integrated circuit. The exact processor of the system can vary. In various embodiments of the present disclosure the processor chip 1502 can be a K20P64M72SF1 from Freescale Semiconductor and is operably connected to an display 1504, pulse switch 1507, buzzer 1508, communication link 1505, power transmitter 1506, touch sensor 1509, detector 1503, and power management chip 1511 as seen in FIG. 16. In such an embodiment the processor 1502 receives power from the power management chip 1511 and executes a timing program thereby pulsing power transmitter 1506. The processor also delivers power via its connection to the display 1504, pulse switch 1507, buzzer 1508, communication link 1505, power transmitter 1506, touch sensor 1509, and detector 1503. The processor 1502 processes the information from the detector 1503 and displays said information on the display 1504. The processor powers up the device via the pulse switch 1507. The processor 1502 transmits information concerning the detector 1503 via the communication link 1505.

The processor runs an application in all embodiments of the present disclosure in which energy is only transmitted by the power transmitter at certain intervals of time. In various embodiments the interval of time for transmitting power can span from microseconds to tens of seconds, greater than about 0.1 seconds but less than about 5 seconds, or greater than about 0.5 seconds but less than about 2 seconds.

The power source 1501 can in various embodiments comprise a variety of components. For example power could be provided by movement of the external device being translated into electrical current as seen in some modern watches. In alternative embodiments the power source can comprise a battery or photovoltaic cell. In various embodiments the power source can comprise a combination of components such as a power management chip 1511 (e.g. MC34704AEPR2 from Freescale Semiconductor), solar cell 1510 (e.g. AM-1801CA from Sanyo Engery), and batter 1512 (e.g. ML-6215/ZTN). In such one embodiment of such a configuration the power management chip 1511 is operably connected to The power transmitter 1506 can in various embodiments comprise a variety of components. In various embodiments the power transmitter can be a laser or LED. In various embodiments the power transmitter can include an LED w/driver 1506 operably connected to the processor chip 1502 as seen in FIG. 16 (e.g. NT-41A0-0482 from Lighting Science Group Corporation).

In various embodiments of the present disclosure, the external device can include a pulse switch 1507 operably connected to the processor 1502 such as TL3315NF250Q from E-switch or others as would be known to those skilled in the art. In various embodiments of the present disclosure the external device can include a touch sensor 1509 operably connected to the processor 1502 such as TSSELEC-TRODEE VM-ND from Freescale Semiconductor or others as would be known to those skilled in the art. In various embodiments of the present disclosure the external device can comprise a buzzer 1508 operably connected to the processor 1502 such as TE-HCS0503A-H2.5 from Tianer Technology. The buzzer 1508 via a signal from the processor 1502 can alert can attempt to wake a user with a low glucose level. When the buzzer 1508 does not wake the used the processor as detected by an interface of the external device by the use, the external device can in various embodiments of the present disclosure send a signal via the communications link 1505 directly or indirectly (via iPhone) to authorities (e.g. 911) to provide aid to the user.

In various embodiments the detector 1503 can be a CCD or an array of CCDs. In various embodiments the 1503 detector can be an array such as TC341-30-ND from Texas Instruments that is operably connected to the processor chip 1502 as seen in FIG. 16.

The detector will have to detect the signal transmitted by the implanted device. Since the signal transmitted by the implanted device can be weaker compared to background noise (e.g. wavelength), the detector has to be able to filter out other wavelengths especially the power transmitter wavelength and the background light. Filtering of the background can be done by measuring the light from a period when the implantable device is not transmitting and subtracting said light from the signal. Filtering of the background can also be accomplished in various embodiments of the present disclosure by means of a physical filter.

In some embodiments the detector will be an array (e.g. of detectors). The array allows the detector to detect a signal from the communication system of the implanted device when the implanted device and the external device are misaligned with respect to the detector. The size of one element of the array can be such as to receive maximum power from the communication signal to optimize the signal to noise ratio. Such array may be designed differently for different applications based on the tissue scattering response in different areas of the body. Also the detector in certain embodiments would have low-noise high-gain front end to detect a potentially weak signal.

The display 1504 of the external device of the system can in various embodiments comprise a watch face, LCD, OLED, or any other means for presenting information from the processor as can be understood by a user (e.g. a color display, mechanical watch hand). In various embodiments the display 1504 can be an LCD display such as C-51847NFJ-SLW-AEN from Kyocera Industrial Ceramics Corporation that is operably connected to the processor chip 1502 as seen in FIG. 16.

The communication link 1505 according to the present invention can comprise a communications means such as but not limited to Bluetooth, USB, and Wi-Fi. In various embodiments the communication link 1505 can be a Bluetooth module such as LMX9830 from Texas instruments that is operably connected to the processor chip 1502 as seen in FIG. 16.

A consumer electronic device is electronic equipment intended for everyday use. Examples include MP3 players, videorecorders, digital cameras, and mobile telephones. In various embodiments the consumer electronic device will be a mobile telephone with a flash as well as a camera element. The dimensions of such a mobile telephone are to be understood to be less than about 1 foot long and less than about 6 inches wide and 4 inches tall.

Figure 13:
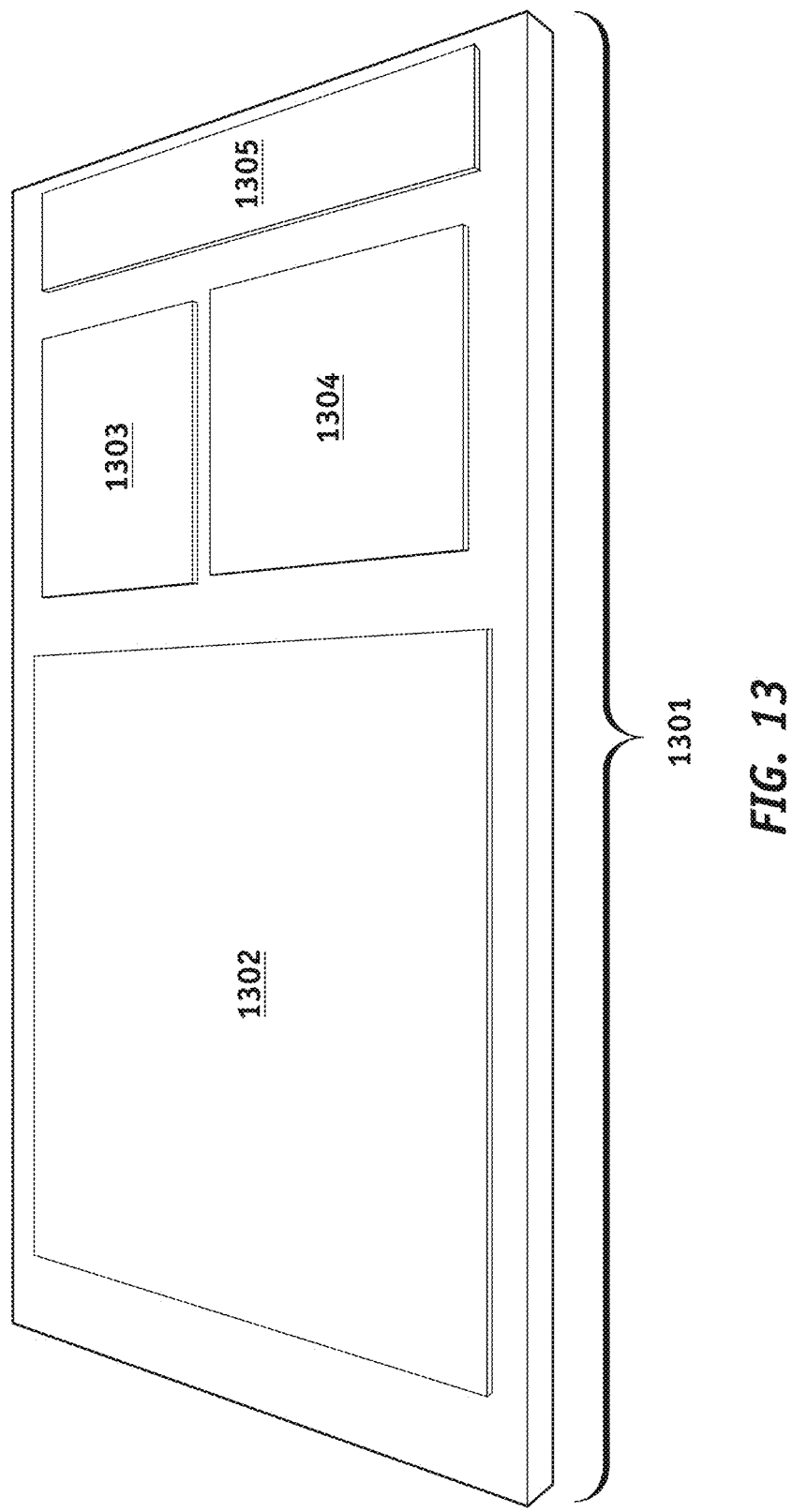
FIG. 13 and FIG. 14 illustrate an exemplary embodiment of the configuration of the external device.
Figure 14:
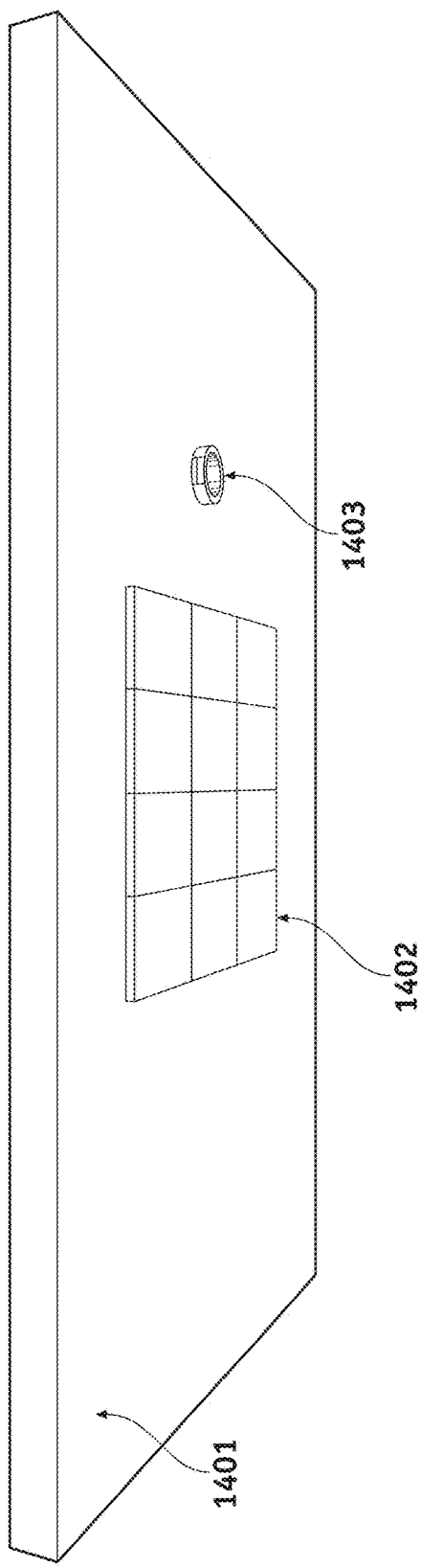
Figure 15:
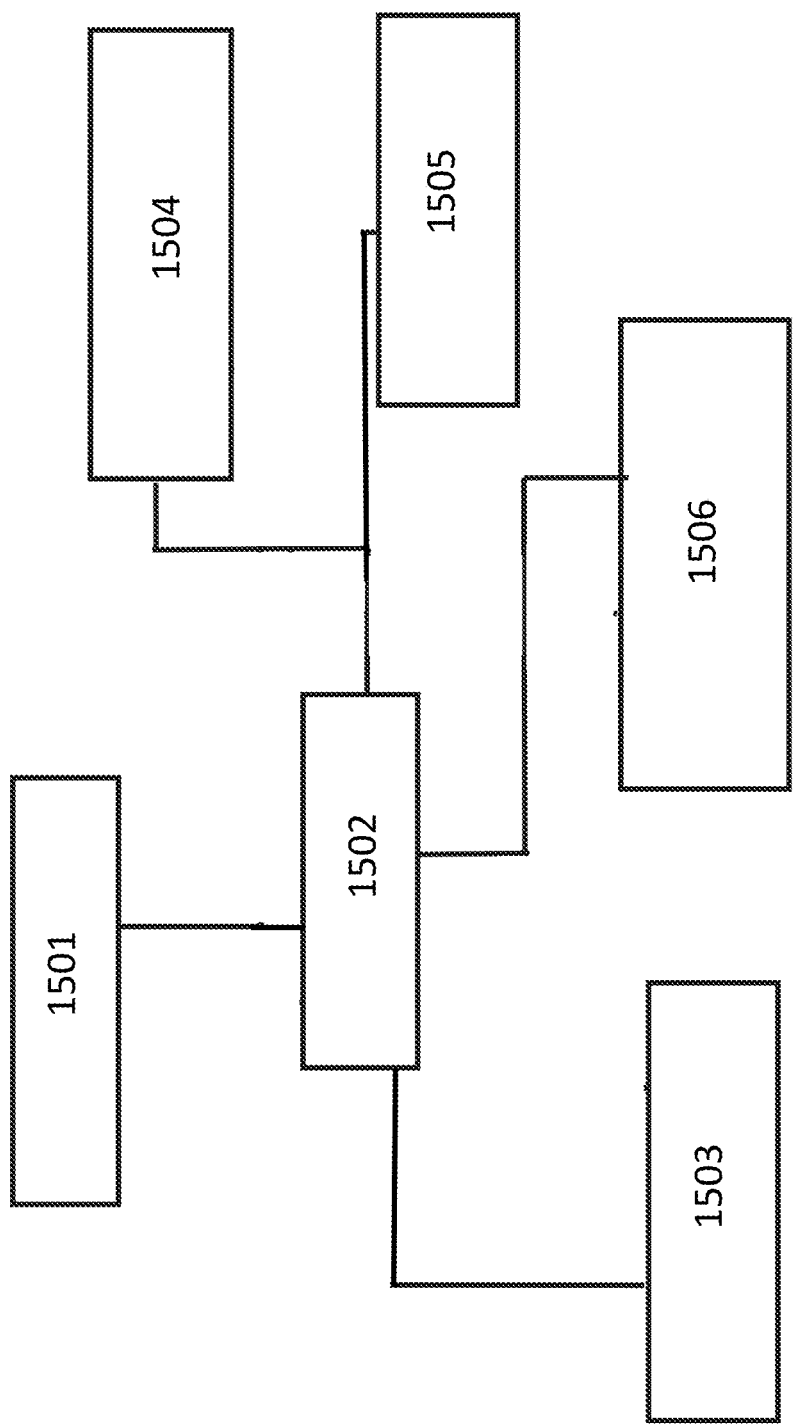
FIG. 15 shows an exemplary block diagram of the external device.

An exemplary embodiment of the present disclosure of the various special configurations of the power transmitter 1403, detector 1402, display 1302, power source 1303, processor 1304 and communication link 1305 can be seen in FIGS. 13 and 14. The display 1302 is on the top side 1301 of the external device and is positioned to the side of a processor 1304, power sources 1303, and communication link 1305. The detector 1402 and the power transmitter 1403 are on the bottom side of the external device. The power transmitter 1403 is positioned distant from the detector 1402 to potentially avoid interference thereof.

EXAMPLES

Optical Testing

Figure 17:
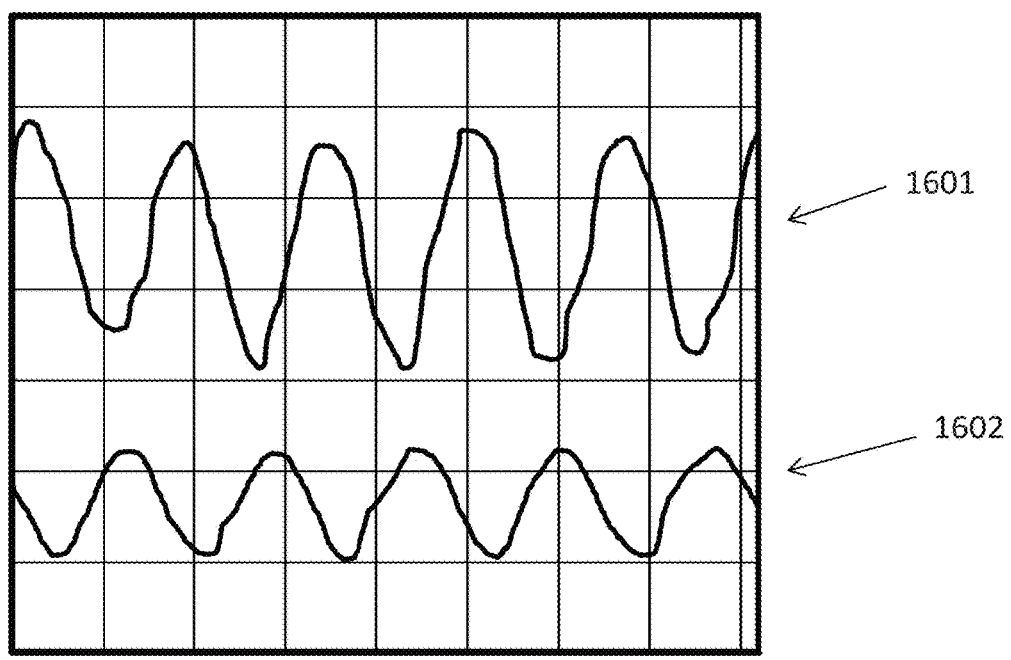
FIG. 17 shows the results of data transmission through tissue.

The inventors tested optical power and optical communication through a 5 mm chicken skin and tissue. The device was placed behind the skin and tissue sample. The device was connected to a functional generator. In front of the skin and tissue sample was positioned a power laser (0.8 w, 800 nm) and a detector (compound semiconductor). In front of the power laser was placed a mechanical shutter. The mechanical shutter was programmed to open for time period of 3 milliseconds with an off time of 1 millisecond. The device received power from the power laser through the tissue sample. Using the power received the device transmitted a sine wave 1601 across the chicken skin and tissue and said signal was received 1602 by the detector as seen in FIG. 17.

Figure 18:
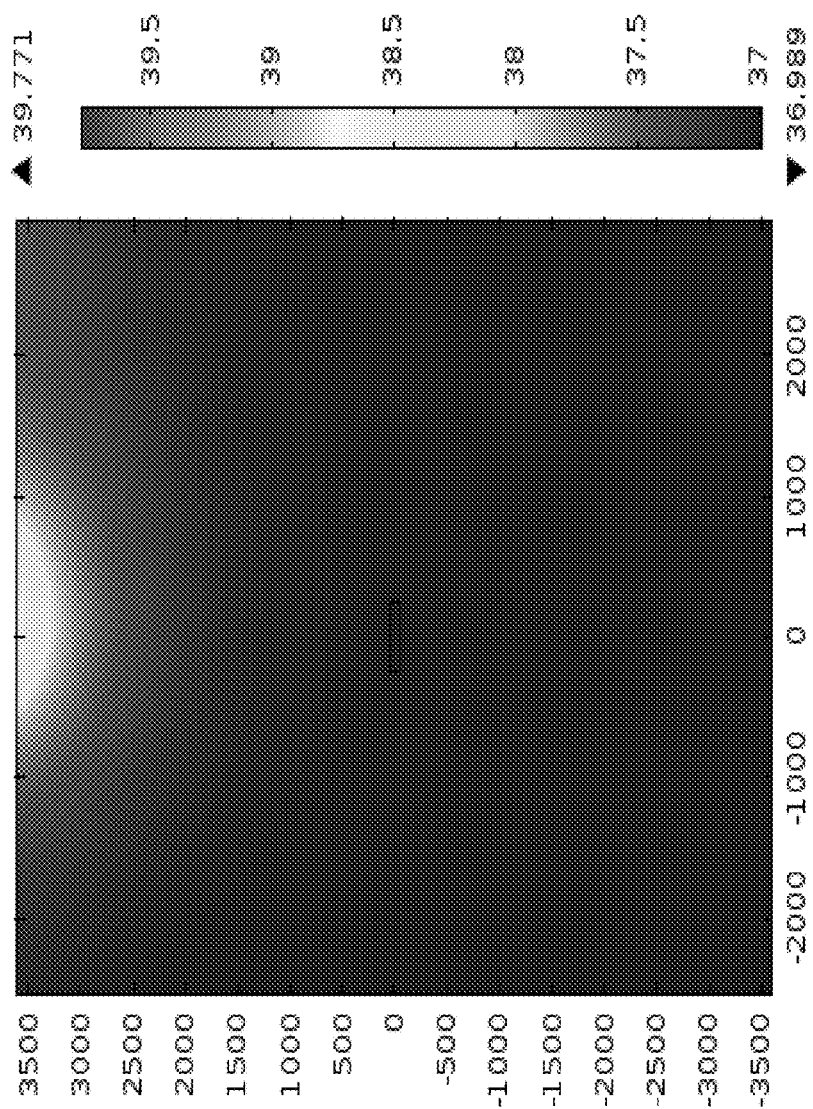
FIG. 18 shows the result of temperature of energy transmission through tissue.

The effect of pulsing and optical power was further evaluated. Specifically, the temperature effect of laser transmission thru tissue was modeled. An implantable device was simulated to be at a 3.5 mm depth inside tissue. In FIG. 18 the vertical and horizontal axis represents distance in microns with the 0 being where the implantable device was located. The side scale of FIG. 18 represents temperature in Celsius correlated to shading. It was found for the specific case of 1 W laser irradiation in the near IR wavelength of 805 nm on the spot of 1 mm square time periods around a second are safe. The 1 W laser was placed above the tissue as in greater than 3500 microns from the implantable device. Times on the orders of 10's of seconds for similar amount of power delivery were found to create temperatures that could potentially cause issue damage.

Glucose Testing

Figure 19:
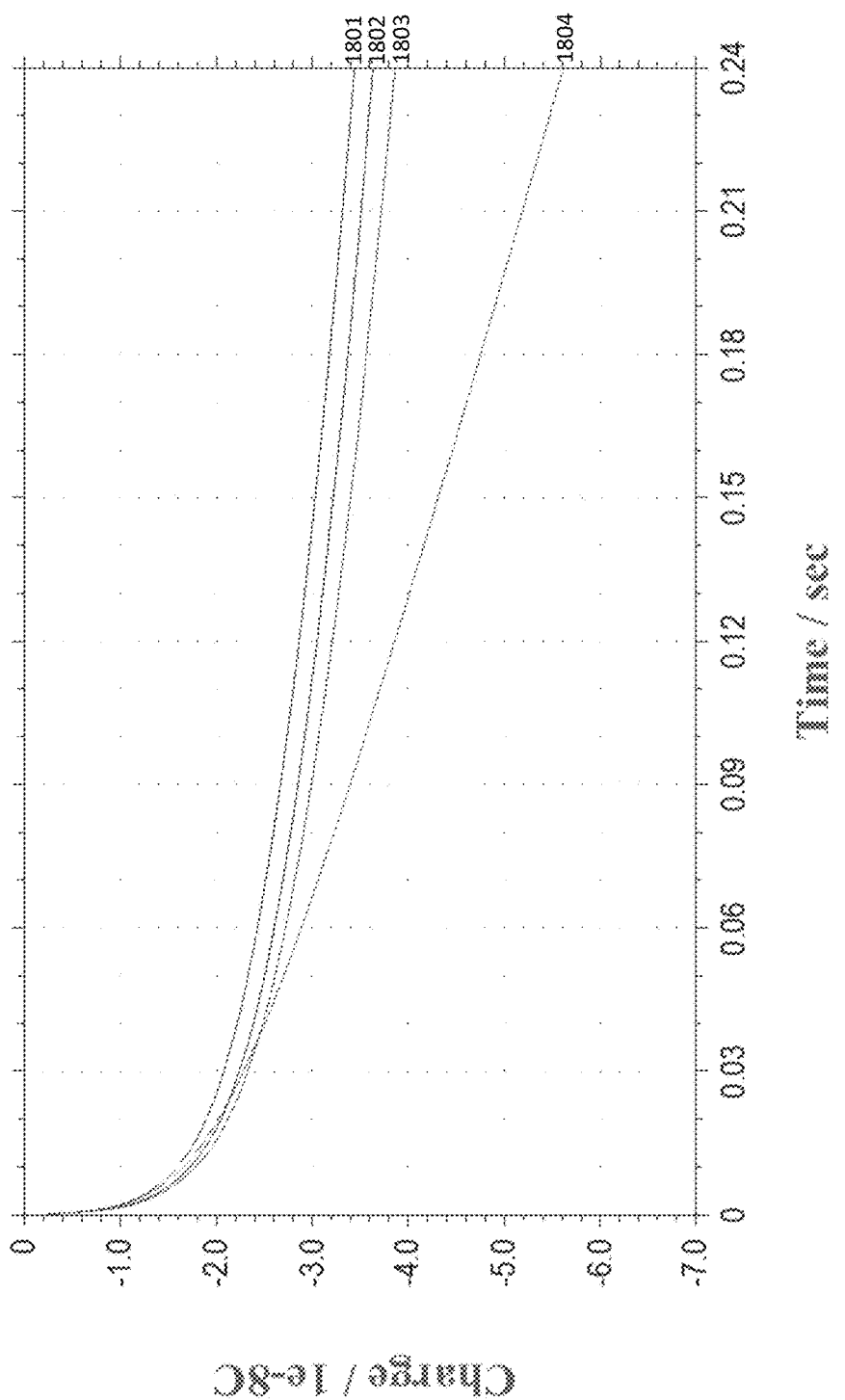
FIG. 19 shows the sensing of glucose levels over the course of short time pulse.
Figure 20:
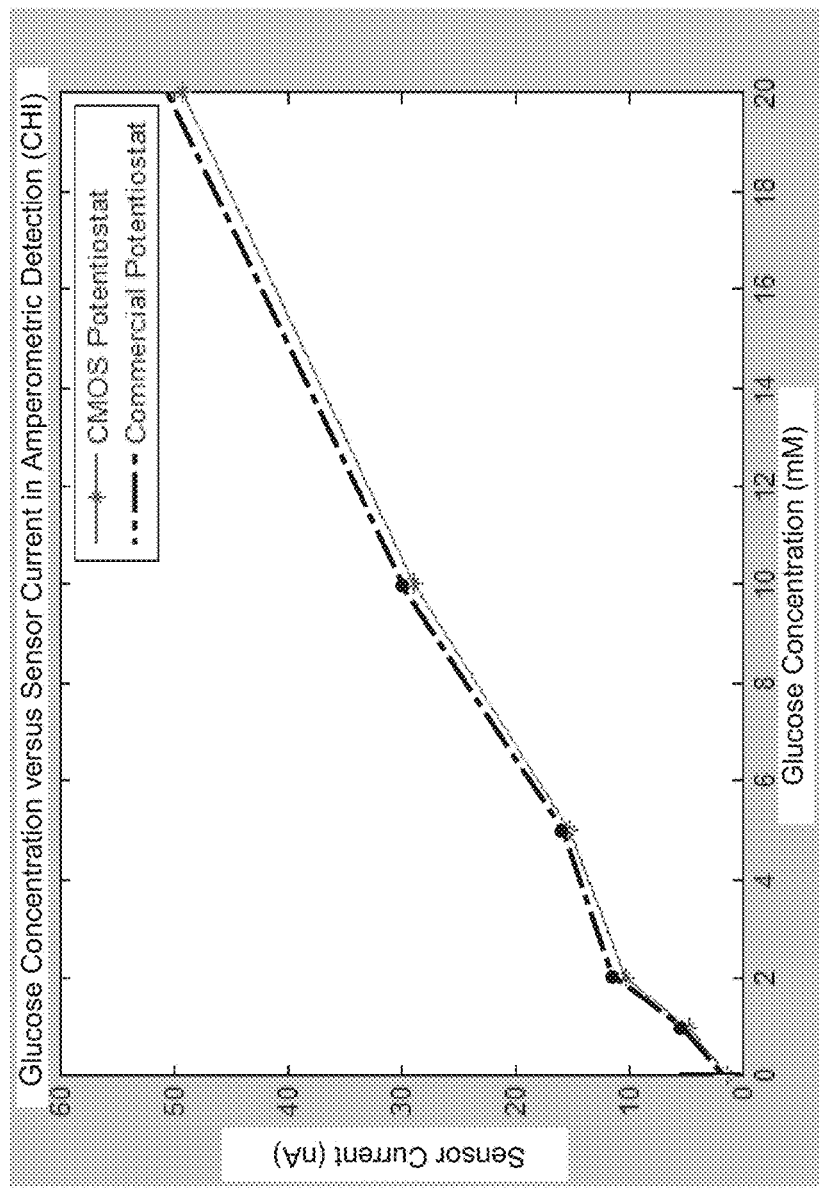
FIG. 20 shows the correlation between current measured by a commercial potentiostat and that of the implantable device.

Glucose testing was performed with phosphate buffer saline solution in a beaker. The sensor was dipped in the solutions carefully so that only the sensor part is exposed to the solution. Insulating epoxy (5 minute epoxy) was used as the material to substantially cover the implantable device. A small vice was used to deploy the epoxy everywhere except the sensor. Solutions with different glucose concentrations, in the physiological range of 0 mM-20 mM, were made. The device was dipped in these solutions and the resulting current from the sensor was measured. The experiment was repeated multiple times for multiple sensors. The sensor was also connected to external electronics (external Potentiostat) to confirm its working. The performance of the device in testing glucose in small time intervals was confirmed in FIG. 19 at three different concentrations 0 mM (1801), 1 mM (1802), 2 mM (1803), and 10 mM (1804). A comparison between the device performance and the performance of an external reference potentiostat CHI 1242B is seen in FIG. 20.

Biological Testing—A Measurement of Foreign Body Capsule Upon Implantation of Foreign Device Formation of a foreign body capsule is a response of the immune system to foreign materials in a living body. The usual outcome of a foreign body capsule is the formation of capsules of tightly-woven collagen fibers, created by the immune response to the presence of foreign objects surgically installed into a living body.

In order to test for the presence or absence of foreign body capsule upon implantation of the device, 3 mice were tested with subcutaneous insertion of the device of the present application which is 500 microns by 500 microns by 200 microns. A second set of 30 mice can then be tested with subcutaneous insertion of a device which was 4000 microns by 4000 microns by 200 microns. Postoperatively, animals can be imaged using live scan micro CT (SkyScan 1176 by Microphotonics) to evaluate the initial shape and orientation of the implants which can be placed at the abdominal region of the mice. Safety assessment can be based on evaluating the biological response to the device and using the live scan micro CT, which can be used to determine that the orientations of the device, the presence of scar tissue formation or foreign body capsule surrounding the implantation device at 0, 3, 6, 0 12, 15 and 18 days.

At 30 days, the mice can then undergo another live scan to examine the presence of foreign body capsule and then the mice can undergo explantation to examine the tissue that surrounds the device.

Potential local effects of the implant can then assessed for abnormal tissue reactions at the time of explantation by macroscopic evaluation of the foreign body capsule tissue surrounding the implant and by histological and cellular morphological analysis of this tissue.

Biological Testing—Capsular Contracture Tissue Histology

Potential local effects of the implanted device can be assessed for abnormal tissue reactions at the time of explantation by macroscopic evaluation of the foreign body capsule tissue surrounding the implant and by histological and cellular morphological analysis of this tissue. The histology of the excised tissue capsules can indicate if the capsules formed show a normal wound-healing response, by examination of the presence of inflammatory cells and can be scored from this (scores of 0 and 1 on a scale of 0 to 5, with 0 being no visible cells in field of view at 400×). Inflammatory cells can include neutrophils, lymphocytes, and macrophages and can then be identified by histological and cellular morphological analysis. Microscopic examination can then be used to show edema, congestion, necrosis, hemorrhage, or granulation of the tissue cells. This can be followed by tissue histology to look for signs of degeneration, bacterial infection, or malignancy in any of the capsules, if the capsules are present.

Biological Testing—Tissue Capsule Thickness

The tissue capsule thickness over the device can be examined for the two groups of mice and can be consistent with the capsule thickness over the entire device. It can be expected that the capsule thickness over the implantable device will range across the mice from the two groups, the mice with the device that is 500 microns by 500 microns by 200 microns and the mice that are implanted with a device that is 4000 microns by 4000 microns by 200 microns. The relative size of the neovascularization bed was scored by assessing the width of the area from the implant/tissue interface to the unaffected areas that had the characteristics of normal tissue and normal vascularity. This is done after 30 days of implantation on the tissue surrounding the explanted device.

The mice with the small 500 microns by 500 microns by 200 microns than the 4000 microns by 4000 microns by 200 microns will be found to have less foreign body capsule formation.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

What is claimed is:

1. An implantable device comprising:
   a communication system;
   a sensor; and
   a monolithic substrate comprising an integrated sensor circuit configured to process input from the sensor into a form conveyable by the communication system, and an integrated power supply configured to receive energy from an external source,
   wherein:
   the communication system is located on a first face of the monolithic substrate and the sensor is located on a second face of the monolithic substrate, the first face being on an opposite side of the monolithic substrate from the second face,
   the monolithic substrate comprises a plurality of holes configured to allow fluid flow from the first face of the monolithic substrate to the second face of the monolithic substrate after implantation of the implantable device,
   the sensor comprises at least one working electrode, at least one reference electrode, and at least one counter electrode,
   the at least one working electrode, the at least one reference electrode, and the at least one counter electrode are high surface area electrodes, each comprising pillars,
   the sensor is an integrated sensor and the monolithic substrate further comprises the integrated sensor, and
   the communication system comprises a laser.

2. The implantable device of claim 1, wherein the monolithic substrate has a height less than 200 microns and a length and width of less than 500 microns.

3. The implantable device of claim 1, wherein the communication system comprises a modulator, an output driver, and a transmission system.

4. The implantable device of claim 3, wherein the modulator comprises a control circuit and a pulse width modulator.

5. The implantable device of claim 1, wherein the at least one working electrode comprises at least two working electrodes.

6. The implantable device of claim 1, wherein the power supply is a photovoltaic power supply.

7. The implantable device of claim 1, wherein the monolithic substrate is a CMOS die.

8. The implantable device of claim 1, further comprising at least one interconnect electrically connecting the sensor to the communication system, through the monolithic substrate.

9. The implantable device of claim 8, wherein the at least one interconnect is cylindrical.

10. The implantable device of claim 1, wherein the sensor is a glucose sensor.

11. A system comprising the implantable device according to claim 1 and an external device, the external device comprising:
- a power source;
- a power transmitter;
- a processor connected to the power transmitter and the power source, the processor configured to pulse power to the implantable device by activating the power transmitter only for an interval of time; and
- a detector that receives information from the communication system of the implantable device.

12. The system according to claim 11 further comprising a communication link to transmit information from the implantable device and operably linked to the detector either directly or through the processor.

13. The system according to claim 11 further comprising a display operably connected to the processor.

14. The system according to claim 11 wherein the detector comprises a detector array.

15. The system according to claim 11 wherein the external device is a consumer electronics device.

* * * * *